(12) United States Patent
Lewis et al.

(10) Patent No.: US 9,371,339 B2
(45) Date of Patent: Jun. 21, 2016

(54) SATURATED AND UNSATURATED SILAHYDROCARBONS VIA IRON AND COBALT PYRIDINE DIIMINE CATALYZED OLEFIN SILYLATION

(71) Applicants: Kenrick Martin Lewis, Flushing, NY (US); Crisita Carmen Hojilla Atienza, Houston, TX (US); Julie L. Boyer, Watervliet, NY (US); Paul J. Chirik, Princeton, NJ (US); Johannes G. P. Delis, Bergen op Zoom (NL); Aroop Kumar Roy, Mechanicville, NY (US)

(72) Inventors: Kenrick Martin Lewis, Flushing, NY (US); Crisita Carmen Hojilla Atienza, Houston, TX (US); Julie L. Boyer, Watervliet, NY (US); Paul J. Chirik, Princeton, NJ (US); Johannes G. P. Delis, Bergen op Zoom (NL); Aroop Kumar Roy, Mechanicville, NY (US)

(73) Assignees: Momentive Performance Materials Inc., Waterford, NY (US); Princeton University, Princeton, NJ (US)

( * ) Notice: Subject to any disclaimer, the term of this patent is extended or adjusted under 35 U.S.C. 154(b) by 0 days.

(21) Appl. No.: 14/243,044

(22) Filed: Apr. 2, 2014

(65) Prior Publication Data

US 2014/0330036 A1 Nov. 6, 2014

Related U.S. Application Data

(60) Provisional application No. 61/819,769, filed on May 6, 2013.

(51) Int. Cl.
| | |
|---|---|
| *C08G 77/20* | (2006.01) |
| *C07F 7/08* | (2006.01) |
| *C07F 15/02* | (2006.01) |
| *C07F 15/06* | (2006.01) |

(52) U.S. Cl.
CPC ............. *C07F 7/0829* (2013.01); *C07F 7/0809* (2013.01); *C07F 7/0896* (2013.01); *C07F 15/02* (2013.01); *C07F 15/025* (2013.01); *C07F 15/06* (2013.01); *C07F 15/065* (2013.01)

(58) Field of Classification Search
USPC .......................... 502/167, 200; 528/31, 32, 33
See application file for complete search history.

(56) References Cited

U.S. PATENT DOCUMENTS

| | | |
|---|---|---|
| 3,159,601 A | 12/1964 | Ashby et al. |
| 3,220,972 A | 11/1965 | Lamoreaux |
| 3,296,291 A | 1/1967 | Chalk et al. |
| 3,775,452 A | 11/1973 | Karstedt |
| 3,928,629 A | 12/1975 | Chandra et al. |
| 4,550,152 A | 10/1985 | Faltynek |
| 4,572,791 A | 2/1986 | Onopchenko et al. |
| 4,578,497 A | 3/1986 | Onopchenko et al. |
| 4,729,821 A | 3/1988 | Timmons et al. |
| 4,788,312 A | 11/1988 | Paciorek et al. |
| 5,026,893 A | 6/1991 | Paciorek |
| 5,166,298 A | 11/1992 | Friedmann et al. |
| 5,331,075 A | 7/1994 | Sumpter et al. |
| 5,432,140 A | 7/1995 | Sumpter et al. |
| 5,866,663 A | 2/1999 | Brookhart et al. |
| 5,955,555 A | 9/1999 | Bennett |
| 6,103,946 A | 8/2000 | Brookhart et al. |
| 6,214,761 B1 | 4/2001 | Bennett |
| 6,265,497 B1 | 7/2001 | Herzig |
| 6,278,011 B1 | 8/2001 | Chen et al. |
| 6,281,303 B1 | 8/2001 | Lavoie et al. |
| 6,297,338 B1 | 10/2001 | Cotts et al. |
| 6,417,305 B2 | 7/2002 | Bennett |
| 6,423,848 B2 | 7/2002 | Bennett |
| 6,432,862 B1 | 8/2002 | Bennett |
| 6,451,939 B1 | 9/2002 | Britovsek |
| 6,455,660 B1 | 9/2002 | Clutton et al. |
| 6,458,739 B1 | 10/2002 | Kimberley et al. |
| 6,458,905 B1 | 10/2002 | Schmidt et al. |
| 6,461,994 B1 | 10/2002 | Gibson et al. |
| 6,472,341 B1 | 10/2002 | Kimberley et al. |
| 6,620,895 B1 | 9/2003 | Cotts et al. |
| 6,657,026 B1 | 12/2003 | Kimberley et al. |
| 7,053,020 B2 | 5/2006 | DeBoer et al. |
| 7,148,304 B2 | 12/2006 | Kimberley et al. |
| 7,161,005 B2 | 1/2007 | Schlingloff et al. |
| 7,247,687 B2 | 7/2007 | Cherkasov et al. |
| 7,268,096 B2 | 9/2007 | Small et al. |
| 7,429,672 B2 | 9/2008 | Lewis et al. |
| 7,442,819 B2 | 10/2008 | Ionkin et al. |

(Continued)

FOREIGN PATENT DOCUMENTS

| | | |
|---|---|---|
| CN | 1727349 | 2/2006 |
| EP | 0786463 | 7/1997 |

(Continued)

OTHER PUBLICATIONS

Archer et al., "Arene Coordination in Bis(imino)pyridine Iron Complexes: Identification of Catalyst Deactivation Pathways in Iron-Catalyzed Hydrogenation and Hydrosilation," Organometallics, vol. 25, pp. 4269-4278 (2006).

(Continued)

*Primary Examiner* — Pancham Bakshi
(74) *Attorney, Agent, or Firm* — Joseph E. Waters; McDonald Hopkins LLC

(57) ABSTRACT

The present invention relates to processes for the synthesis of saturated and unsaturated silahydrocarbons using iron-containing or cobalt-containing catalysts. The processes of the invention can produce tetraalkylsilanes, phenyltrialkylsilanes, substituted phenyltrialkylsilanes and their mixtures, which are useful as lubricants and hydraulic fluids, as well as alkyl alkenylsilanes, phenyl alkenylsilanes and substituted phenyl alkenylsilanes and their mixtures, which are useful in the synthesis of saturated silahydrocarbons and other organofunctional silanes.

20 Claims, No Drawings

(56) References Cited

U.S. PATENT DOCUMENTS

| | | | |
|---|---|---|---|
| 7,456,285 | B2 | 11/2008 | Schlingloff et al. |
| 7,696,269 | B2 | 4/2010 | Cruse et al. |
| 8,236,915 | B2 * | 8/2012 | Delis et al. ............... 528/14 |
| 8,415,443 | B2 | 4/2013 | Delis et al. |
| 2002/0058584 | A1 | 5/2002 | Bennett |
| 2006/0263675 | A1 | 11/2006 | Adzic et al. |
| 2007/0264189 | A1 | 11/2007 | Adzic et al. |
| 2008/0262225 | A1 | 10/2008 | Schlingloff et al. |
| 2008/0293878 | A1 | 11/2008 | Funk et al. |
| 2009/0068282 | A1 | 3/2009 | Schlingloff et al. |
| 2009/0296195 | A1 | 12/2009 | Fontana et al. |
| 2011/0009565 | A1 | 1/2011 | Delis et al. |
| 2011/0009573 | A1 | 1/2011 | Delis et al. |
| 2012/0130021 | A1 | 5/2012 | Tondreau et al. |
| 2012/0130105 | A1 | 5/2012 | Lewis et al. |
| 2012/0130106 | A1 | 5/2012 | Lewis et al. |
| 2013/0158281 | A1 | 6/2013 | Weller et al. |
| 2014/0051822 | A1 | 2/2014 | Atienza et al. |
| 2014/0243486 | A1 | 8/2014 | Roy et al. |
| 2014/0330024 | A1 | 11/2014 | Atienza et al. |
| 2014/0330036 | A1 | 11/2014 | Lewis et al. |
| 2014/0343311 | A1 | 11/2014 | Boyer et al. |
| 2015/0080536 | A1 | 3/2015 | Diao et al. |
| 2015/0137033 | A1 | 5/2015 | Diao et al. |

FOREIGN PATENT DOCUMENTS

| | | |
|---|---|---|
| GB | 2013207 | 8/1979 |
| TW | 200902541 | 1/2009 |
| WO | 9210544 | 6/1992 |
| WO | 02088289 | 11/2002 |
| WO | 03042131 | 5/2003 |
| WO | 2008085453 | 7/2008 |
| WO | 2011006044 | 1/2011 |
| WO | 2012/007139 | 1/2012 |
| WO | 2012071359 | 5/2012 |
| WO | 2013/043783 | 3/2013 |
| WO | 2013043846 | 3/2013 |

OTHER PUBLICATIONS

Bowman et al., "Reduced N-Alkyl Substituted Bis(imino)pyridine Cobalt Complexes: Molecular and Electronic Structures for Compounds Varying by Three Oxidation States," Inorg. Chem. 2010, 49, 6110-6123, Germany.

Zhu et al., "A Measure for *-Donor and *-Acceptor Properties of Diiminepyridine-Type Ligands," Organometallics 2008, 27, 2699-2705.

Zhu et al., "(Py)2Co(CH2SiMe3)2 As an Easily Accessible Source of "CoR2"," Organometallics, 2010, 29 (8), 1897-1908.

Yeung, et al., "Cobalt and iron complexes of chiral Cl- and C2-terpyridines: Synthesis, characterizationa dn use in catalytic asymmetric cyclopropanation of styrenes." Inorganica Chimica Acta 362 (2009) 3267-3273.

Bart et al., "Electronic Structure of Bis(imino)pyridine Iron Dichloride, Monochloride, and Neutral Ligand Complexes: A Combined Structural, Spectroscopic, and Computational Study," J. Am. Chem. Soc. 2006, 128, 13901-13912.

Bart et al., "Preparation and Molecular and Electronic Structures of Iron(0) Dinitrogen and Silane Complexes and Their Application to Catalytic Hydrogenation and Hydrosilation," Journal of the American Chemical Society, vol. 126, pp. 13794-13807 (2004).

Connelly et al., "Chemical Redox Agents for Organometallic Chemistry," Chem. Rev. 1996, 96, 877-910.

Atienza et al. "Synthesis, Electronic Structure, and Ethylene Polymerization Activity of Bis(imino)pyridine Cobalt Alkyl Cations," Agnewandte Chem. Int. Ed. 2011, 50, 8143-8147.

Glatz et al., "Terpyridine-Based Silica Supports Prepared by Ring-Opening Metathesis Polymerization for the Selective Extraction of Noble Metals," Journal of Chromatography A, vol. 1015, pp. 65-71 (2003).

Nagashima et al., "Dehydrogenative Silylation of Ketones with a Bifunctional Organosilane by Rhodium-Pybox Catalysts," Chem. Soc. of Jpn., Chemistry Letters, 1993, 347-350, Toyohashi, Aichi 441.

Hosokawa et al., "A Chiral Iron Complex Containing a Bis(oxazolinyl)phenyl Ligand: Preparation and Asymmetric Hydrosilylation of Ketones," Organometallics, 29, 5773-5775 (2010).

Bouwkamp, "Iron-Catalyzed [$2\pi+2\pi$] Cycloaddition of a,$\omega$-Dienes the Importance of Redox-Active Supporting Ligands" Journal of the American Chemical Society, 2006, V128 N41, P13340-13341.

Kim et al., "2,2':6',2"-Terpyridine and Bis(2,2':6',2"-terpyridine)Ruthenium(II) Complex on the Dendritic Periphery," Journal of Organometallic Chemistry, vol. 673, pp. 77-83 (2003).

Kroll et al., "Access to Heterogeneous Atom-Transfer Radical Polymerization (ATRP) Catalysts Based on Dipyridylamine and Terpyridine via Ring-Opening Metathesis Polymerization (ROMP)," Macromolecular Chemistry and Physics, vol. 202, pp. 645-653 (2001).

Field et al., "One-Pot Tandem Hydroamination/Hydrosilation Catalyzed by Cationic Iridium(I) Complexes," Organometallics, vol. 22, pp. 4393-4395, Sep. 25, 2003.

Dekamin et al., "Organocatalytic, rapid and facile cyclotrimerization of isocyanates using tetrabutylammonium phthalimide-N-oxyl and tetraethylammonium 2-(carbamoyl) benzoate under solvent-free conditions," Catalysis Communications 12 (2010) 226-230.

Nesmeyanov et al., "Addition, Substitution, and Telomerization Reactions of Olefins in the Presence of Metal Carbonyls or Colloidal Iron," Tetrahedron, vol. 17, pp. 61-68 (1962).

Pal, et al., "Preparation and hydrosilylation activity of a molybdenum carbonyl complex that features a pentadentate bis (amino)pyridine lignad," Inorg Chem. Sep. 2, 2014; 53(17):9357-65. doi: 10.1021/ic501465v. Epub Aug. 20, 2014.

Jairam et al., "Ester Hydrolysis with 2,6-di(pyrazol-3-yl)pyridines and their Co 11 Complexes in Homogeneous and Micellar Media," Journal of Inorganic Biochemistry 84, 2001, 113-118, Toronto, Ontario, Canada.

Buschbeck et al., "Triethylene Glycol Ether End-grafted Carbosilane Dendrimers: Synthesis and Complexation Behavior," Inorganic Chemistry Communications, vol. 7, pp. 1213-1216, Oct. 13, 2004.

Seckin, "Preparation and Catalytic Properties of a Ru(II) Coordinated Polyimide Supported by a Ligand Containing Terpyridine Units," Journal of Inorganic and Organometallic Polymers and Materials, Apr. 9, 2009, 19(2), 143-151.

Sieh et al., "Metal-Ligand Electron Transfer in 4d and 5d Group 9 Transition Metal Complexes with Pyridine, Diimine Ligands," Eur. J. Inorg. Chem., 2012:444-462. doi 10.1002/ejic.201101072.

Speier et al., "The Addition of Silicon Hydrides to Olefinic Double Bonds. Part II. The Use of Group VIII Metal Catalysts," Journal of the American Chemical Society, vol. 79, pp. 974-979 (1956).

Thammavongsy et al., Ligand-Based Reduction of CO2 and Release of CO and Iron(II). Inorg. Chem., 2012, 51 (17), pp. 9168-9170. DOI: 10:1021/ic3015404. Publication Date (Web): Aug. 20, 2012.

Timpa, "Non-Innocent Pyridine Based Pincer Ligands and Their Role Catalysis" Nov. 1, 2010.

Tondreau, et al., "Enantiopure Pyridine Bis(oxazoline) "Pybox" and Bis(oxazoline) "Box" iron Dialkyl Complexes: Comparison to Bis(imino)pyridine Compounds and Application to Catalytic Hydrosilylation of Ketones," Organometallics, Jun. 9, 2009, 28(13), 3928-3940.

Tondreau, et al "Synthesis and electronic structure of cationic, neutral, and anionic bis (imino)pyridine iron alkyl complexes: evaluation of redox activity in single-component ethylene polymerization catalysts." J Am Chem Soc. Oct. 27, 2010; 132(42): 15046-59. doi: 10.1021/ja106575b.

Gibson et al., "The nature of the active species in bis(imino)pyridyl cobalt ethylene polymerisation catalysts," Chem. Commun., 2001, 2252-2253.

Wile, et al. "Reduction chemistry of aryl- and alkyl-substituted bis(imino)pyridine iron dihalide compounds: molecular and electronic structures of [(PDI)2Fe] derivatives." Inorg Chem May 4, 2009; 48(9):4190-200.

(56) References Cited

OTHER PUBLICATIONS

Tondreau, et al., "Iron Catalysts for Selective Anti-Markovnikov Alkene Hydrosilylation Using Tertiary Silanes," Science, vol. 335, No. 6068, Feb. 2, 2012. pp. 567-570.
Abu-Surrah et al., "New bis(imino)pyridine-iron(II)- and cobalt(II)-based catalysts: synthesis, characterization and activity towards polymerization of ethylene" Journal of Organometallic Chemistry 648 (2002) 55-61.
Albon et al., "Metal Carbonyl Complexes Involving 2,6Bix[I-(phenylimino)ethyl]pyridine; Bidentate Corrdination of a Potentially Tridentate Ligand" Inorganica Chimica Acta, 159 (1989) 19-22.
Alyea et al., "Terdentate NNN Donor Ligands Derived from 2,6-Diacetylpyridine" Syn. React. Inorg. Metal-Org. Chem., 4(6), 535-544 (1974).
Bouwkamp, "Iron-Catalyzed [2π+2π] Cycloaddition of α,ω-Dienes the Importance of Redox-Active Supporting Ligands" Journal of the American Chemical Society, 2006, V128 N41, P13340-13341.
Britovsek et al., "Novel Olefin Polymerization Catalysts Based on Iron and Cobalt," Chem. Commun., 1998, 849-850.
Cetinkaya et al., "Ruthenium(ii) complexes with 2,6-pyridyl-diimine ligands: synthesis, characterization and catalytic activity in epoxidation reactions" Journal of Molecular Catalysis A: Chemical 142 (1999) 101-112.
Corey et al., "Reactions of Hydrosilanes with Transition-Metal Complexes: Formation of Stable Transition-Metal Silyl Compounds," Journal of Chemical Reviews, vol. 99, pp. 175-292 (1999).
Haarman et al., "Reactions of [RhCI(diene)]2 with Bi- and Terdentate Nitrogen Ligands. X-ray Structures of Five-Coordinate Complexes," Am. Chem. Soc., Organometallics 1997, 16, 54-67.
Kickelbick et al., New J. Chem., 2002, 26, 462-468.
Kooistra et al., Inorganica Chimica Acta 357 (2004) 2945-2952.
Lapointe, et al., "Mechanistic Studies of Palladium(II)-Catalyzed Hydrosiliation and Dehydrogenative Silation Reactions," J. Amer. Chem. Soc. 119 (1997), pp. 906-917.
Lewis et al., "Hydrosilylation Catalized by Metal Colloids: A Relative Activity Study," Organometallics, 9 (1990), 621-625.
Lions et al., J. Chem. Soc. (A) 1957, vol. 79, 2733-2738.
Lu et al., "The Molecular Structure of a Complex of a 2,6-Diimino-Pyridine as a Bidentate Liandd with Molybdenum Carbonyl" Inorganica Chimica Acta, 134 (1987) 229-232.
Pangborn et al., "Safe and Convenient Procedure for Solvent Purification," Oraganometallics, 15:1518 (1996).
Randolph, Claudia L. et al., "Photochemical Reactions of (η5-Pentamethylcyclopentadienyl)dicarbonyliron-Alkyl and Silyl Complexes: Reversible Ethylene Insertion into an Iron-Silicon Bond and Implications for the Mechanism of Transition-Metal-Catalyzed Hydrosilation of Alkenes," Journal of The American Chemical Society, vol. 108, pp. 3366-3374 (1986).
Russell et al., "Synthesis of Aryl-Substituted Bis(imino)pyridine Iron Dinitrogen Complexes," Inorg. Chem. 2010, 49, 2782-2792.
Sacconi et al., "High-spin Five-Co-Ordinate Nickel (II) and Cobald (II) Complexes with 2,6-Diacetylepyridinebis (imines)," J. Chem. Soc. (A), 1968, 1510-1515.
Tondreau et al., "Bis(imino)pyridine Iron Complexes for Aldehyde and Ketone Hydrosilylation," Am. Chem. Soc., 2008, vol. 10, No. 13, 2789-2792.
Woo et al., "Redistribution of Bos- and Tris(silyl)methanes Catalyzed by Red-Al," Bull. Korean. Chem. Soc. 1996, 17, 123-125.
Wu et al., "A Strategy for the Synthesis of Well-Defined Iron Catalysts and Application to Regioselective Diene Hydrosilylation," Journal of the American Chemical Society, vol. 132, No. 38. Sep. 29, 2010, pp. 13214-13216.
Yi, Chae S. et al., "Regioselective Intermolecular Coupling Reaction of Arylketones and Alkenes Involving C-H Bond Activation Catalyzed by an in Situ Formed Cationic Ruthenium Hydride Complex," Organometallics, vol. 28, pp. 4266-4268 (2009).
Zhang et al., "Ferrous and Cobaltous Chlorides Bearing 2,8-Bis(imino)quinolines: Highly Active Catalysts for Ethylene Polymerization at High Temperature," Organometallics, vol. 29, pp. 1168-1173 (2010).
International Preliminary Report on Patentability for PCT/US2014/36942 dated Nov. 10, 2015.
International Search Report and Written Opinion of the International Searching Authority for PCT/US2014/36942 mailed Aug. 26, 2014.
Toma et al., J. Braz. Chem. Soc., vol. 7, No. 6, 391-394, 1996.
Suzuki, et al., "Random and block copolymerizations of norbornene with conjugated 1,3-dienes catalyzed by novel No compounds involving N- or O-donated ligands" Reactive & Functional Polymers 59 (2004) 253-266, May 6, 2004.
Seki et al., "Single-Operation Synthesis of Vinyl silanes from Alkenes and Hydrosilanes with the Aid of Ru (CO)12," Am. Chem. Soc., J. Org. Chem. 1986, 51, 3890-3895, Osaka, Japan.
Oro et al. "Hydrosilylation of Alkenese by Iridium Complexes," J. Mol. Catalysis, 1986, 37, 151-156.
Naumov et al., "Selective Dehydrogentative Silylation-Hydrogenation Reaction of Divinyldisiloxane with Hydrosilane Catalyzed by an Iron Complex," Journal of the American Chemical Society, 2012, vol. 134, Issue 2, 804-807, Osaka, Japan.
McAtee et al., "Preparation of Allyl and Vinyl Silanes by the Palladium-Catalyzed Silylation of Terminal Olefins: A Silyl-Heck Reaction**," Angewandte Chemie, Int. Ed. 2012, 51, 3663-3667.
Marciniec et al., "Competitve silylation of olefins with vinylsilanes and hydrosilanes photocatalyzed by iron carbonyl complexes," Inorg. Chem. Commun. 2000, 3, 371.
Lu et al., "Iridium-Catalyzed (Z)-Trialkylsilylation ofTerminal Olefins," J. Org. Chem, 2010, 75, 1701-1705, Dallas, Texas.
Kuo, et al., "Electrochemical studies of nickel bis(2,2':6',2"-terpyridine) with alkyl/aryl/allyl bromides and activeated olefins in nonaqueous solvents" Jiemian Kexue Huishi, vol. 15, Issue 1, pp. 23-42, Journal, 1992, Coden: CMKCEW, ISSN: 1026-325X.
Kakiuchi et al., "Dehydrogenative Silylation of 1,5-Dienes with Hydrosilanes Catalyzed by RhCI (PPh3)3," Am. Chem. Soc., Organometallics, 1993, 12, 4748-4750, Kagawa, Japan.
Kakiuchi et al., "Completely Selective Synthesis of (E)-B-(triethylsilyl)styrenes by Fe3(CO)12-catalyzed Reaction of Styrenes With Triethylsilane," Journal of Organometallic Chemistry 1993, 456, 45-47, Osaka, Japan.
Humphries et al., "Investigations into the Mechanism of Activation and Initiation of Ethylene Polymerization by Bis (imino)pyridine Cobalt Catalysts: Synthesis, Structures, and Deuterium Labeling Studies," Organometallics 2005, 24, 2039-2050, London, United Kingdom.
Fernandez et al., "Synthesis and Reactions of Dihydrido(triethylallyl)(1,5-cyclooctadiene)-Iridium(III) Complexes: Catalysts for Dehydrogneative Silylation of Alkenese," Organometallics, 1986, 5, 1519-1520.
Chen et al., "General Synthesis of Di-u-oxo Dimanganese Complexes as Functional Models for the Oxygen Evolving complex of Photosystem II" Inorg. Chem. 2005, 44, 7661-7670.
Bowman et al, "Synthesis and Molecular and Electronic Structures of Reduced Bis(imino) pyridine Cobalt Dinitrogen Complexes: Ligand versus Metal Reduction," J. Am. Chem. Soc., 2010, 132, 1676-1684, Germany.
Atienza, et al., "Olefin hydrosilylation and dehydrogenative silylation with bis(imino) pyridine iron and cobalt catalysts," Abstracts of Papers, 244th ACS National Meeting & Exposition, Philadelphia, PA, Aug. 19-23, 2012.
Atienza, "Reactivity of Bis(Iminio)Pyridine Cobalt Complexes in C—H Bond Activation and Catalytic C—C and C—Si Bond Formation" PhD thesis, Jun. 2013, Princeton University.
Shaikh et al., "Iron-Catalyzed Enantioselevtive Hydrosilylation of Keytones," Angew. Chem. Int. Ed., 2008, 47, 2497-2501.
De Bo et al., "Hydrosilylation of Alkynes Mediated by N-heterocyclic Carben Platinum(0) Complexes," Organometallics, 2006, 25, 1881-1890.
Boudjouk et al., "Exclusive β-hydrosilylation of acrylates catalysed by copper-tetramethylethylenediamine," Journal of Organometallic Chemistry, Jan. 1, 1993, pp. 41-43.
Brookhart et al., "Mechanism of a cobalt(III)-catalyzed olefin hydrosilation reaction: direct evidence for a silyl migration pathway," J. Am. Chem. Soc. 1993, 115, 2151.

(56) References Cited

OTHER PUBLICATIONS

Castro, Pascel M. et al., "Iron-Based Catalysts Bearing Bis(imido)-Pyridine Ligands for the Polymerization of tert-Butyl Acrylate," Journal of Polymer Science: Part A: Polymer Chemistry, vol. 41, pp. 1380-1389 (2003).

Cornish, et al., "Homogeneous catalysis: VI. Hydrosilylation using tri(pentanedionato)rhodium(III) or tetrakis(μ-acetato) Dirhodium(II) as Catalysts," Journal of Organometallic Chemistry, Elsevier-Sequoia S.A. Lausanne, CH, vol. 172, No. 2, Jun. 12, 1979, pp. 153-163.

Chuit et al. "Reactivity of penta- and hexacoordinate silicon compounds and their role as reaction intermediates," Chem. Rev. 1993, 93, 1371-1448.

De Rycke et al., "Toward reactant encapsulation for substrate-selectivity," Tetrahedron Lett. 2012, 53, 462.

Doucette, "Homogeneous Iron Catalysts With Redox-Active Ligands: Synthesis and Electronic Structure," Dissertation Cornell University, Aug. 2006.

Doyle et al., "Addition/Elimination in the Rhodium(II) Perfluorobutyrate Catalyzed Hydrosilylationo of 1-Alkenes. Rhodium Hydride Promoted Isomerization and Hydrogenation," Organometallics, 1992, 11, 549-555, San Antonio, Texas.

Falck, J. R. et al. "Iridium-Catalyzed (Z)-Trialkylsilylation of Terminal Olefins," J. Org. Chem. 2010, 75, 1701.

Figgins et al., "Complexes of Iron(II), Cobalt(II) and Nickel(II) with Biacetyl-bis-methlylimine, 20Pyridinal-methylimine and 2,6-Pyridindial-bis-methylimine" J. Am. Chem. Soc. 1960, vol. 82, 820-824.

Gandon, et al., "Silicon-Hydrogen Bond Activation and Hydrosilylation of Alkenes Mediated by CpCo Complexes: A Theoretical Study," J. Am. Chem. Soc. 2009, 131, 3007.

Hori et al., "Ruthenium Complex-Catalyzed Silylation of Olefins. Selective Sysnthesis of Allysilanes," Bull. Chem. Soc. Jpn., 1988, 61, 3011-3013, Kyoto, Japan.

Itoh et al., "Disproportionation reactions of organohydrosilanes in the presence of base catalysts" J. Organomet. Chem., 2001, 629, 1-6.

Ivchenko et al., "A convenient approach for the synthesis of 2,6-diformyl- and 2,6-diacetylpyridines," Tetrahedron Lett. 2013, 54, 217.

Fruchtel et al; "Organic Chemistry on Solid Supports," Angewandte Chemie International Edition in English, 1996, vol. 35, Issue 1, pates 17-42.

Junge et al., "Iron-Catalyzed Reducation of Carboxylic Esters to Alcohols," European Journal of Organic Chemistry, vol. 2013, No. 11, Mar. 1, 2013, pp. 2016-2065.

Knijnenburg et al., "Olefin hydrogenation using diimine pyridine complexes of Co and Rh," Journal of Molecular Catalysis, 232 (2005), No. 1-2, pp. 151-159.

Marciniec, Bogdan, "Catalysis by Transition Metal Complexes of Alkene Silylation—Recent Progress and Mechanistic Implications," Coordination Chemistry Reviews, 249 (2009) 2374-2390.

Marciniec et al. "Encyclopedia of Catalysis" pp. 6, 7, and 20, Mar. 5, 2010.

Martinez, Remi et al., "C—C Bond Formation via C—H Bond Activation Using an in Situ-Generated Ruthenium Catalyst," Journal of the American Chemical Society, vol. 131, pp. 7887-7895 (2009).

McAtee et al, "Rational Design of a Second Generation Catalyst for Preparation of Allylsilanes Using the Silyl-Heck Reaction," J. Am. Chem. Soc. 2014, 136 (28), 10166-10172.

Bareille et al., "First Titanium-Catalyzed anti-1,4-Hydrosilylation of Dienes," Organometallics, 2005, 24(24), 5802-5806.

Nishiyama et al., "An Iron-Catalysed Hydrosilylation of Ketones," Chem. Commun., Royal Society of Chemistry, 2007, 760-762.

Furuta et al., "Highly efficient catalytic system for hydrosilylation of ketones with iron(II) acetate—thiophenecarboxylate," Tetrahedron Letters, 2008, vol. 49, Issue 1, pp. 110-113.

Ojima et al., "Regioselective hydrosilylation of 1,3-dienes catalyzed by phosphine complexes of palladium and rhodium," J. Organomet. Chem. 1978, 157, 359-372.

Pettigrew, "Synthetic Lubricants and High Performance Fluids, Ch. 12 Silahydrcarbons" (second edition), L. R. Rudnick and L R. Shubkin (Editors), Marcel Dekker, NY 1999, pp. 287-296.

Poyatos, Macarena et al., "Coordination Chemistry of a Modular N,C-Chelating Oxazole-Carbene Ligand and Its Applications in Hydrosilylation Catalysis," Organometallics, vol. 25, pp. 2634-2641 (2006).

Reiff, W. M. et al., "Mono(2,2',2"-terpyridine) Complexes of Iron(II)," Journal of Inorganic Chemistry, vol. 8, No. 9, pp. 2019-2021 (1969).

Parker et al. "1,2-Selective Hydrosilylation of Conjugated Dienes," J. Am. Chem. Soc., 2014, 136 (13), pp. 4857-4860.

* cited by examiner

SATURATED AND UNSATURATED SILAHYDROCARBONS VIA IRON AND COBALT PYRIDINE DIIMINE CATALYZED OLEFIN SILYLATION

CROSS-REFERENCE TO RELATED APPLICATIONS

This application claims the benefit of U.S. Provisional Application Ser. No. 61/819,769 filed May 6, 2013, which is incorporated by reference herein in its entirety.

FIELD OF THE INVENTION

The present invention relates to processes for the synthesis of saturated and unsaturated silahydrocarbons using iron-containing or cobalt-containing catalysts. The processes of the invention can produce tetraalkylsilanes, phenyltrialkylsilanes, substituted phenyltrialkylsilanes and their mixtures, which are useful as lubricants and hydraulic fluids, as well as alkyl alkenylsilanes, phenyl alkenylsilanes and substituted phenyl alkenylsilanes and their mixtures, which are useful in the synthesis of saturated silahydrocarbons and other organofunctional silanes.

BACKGROUND OF THE INVENTION

Hydrosilylation chemistry, typically involving a reaction between a silyl hydride and an unsaturated organic group, is one basic route in the synthesis of commercial silicone-based products like silicone surfactants, silicone fluids and silanes, as well as many addition cured products like sealants, adhesives, and silicone-based coating products. Heretofore, hydrosilylation reactions have been typically catalyzed by precious metal catalysts, such as platinum or rhodium metal complexes.

Various precious metal complex catalysts are known in the art. For example, U.S. Pat. No. 3,775,452 discloses a platinum complex containing unsaturated siloxanes as ligands. This type of catalyst is known as Karstedt's-catalyst. Other exemplary platinum-based hydrosilylation catalysts that have been described in the literature include Ashby's catalyst as disclosed in U.S. Pat. No. 3,159,601, Lamoreaux's catalyst as disclosed in U.S. Pat. No. 3,220,972, and Speier's catalyst as disclosed in Speier, J. L, Webster J. A. and Barnes G. H., J. Am. Chem. Soc. 79, 974 (1957).

Although these precious metal complex catalysts are widely accepted as catalysts for hydrosilylation reactions, they have several distinct disadvantages. One disadvantage is that the precious metal complex catalysts are inefficient in catalyzing certain reactions. For example, in the case of hydrosilylations of allyl polyethers with silicone hydrides using precious metal complex catalysts, use of an excess amount of allyl polyether, relative to the amount of silicone hydride, is needed to compensate for the lack of efficiency of the catalyst in order to ensure complete conversion of the silicone hydride to a useful product. When the hydrosilylation reaction is completed, this excess allyl polyether must either be: (A) removed by an additional step, which is not cost-effective, or (B) left in the product which results in reduced performance of this product in end-use applications. Additionally, the use of an excess amount of allyl polyether typically results in a significant amount of undesired side products such as olefin isomers, which in turn can lead to the formation of undesirably odoriferous byproduct compounds.

Another disadvantage of the precious metal complex catalysts is that sometimes they are not effective in catalyzing hydrosilylation reactions involving certain type of reactants. It is known that precious metal complex catalysts are susceptible to catalyst poisons such as phosphorous and amine compounds. Accordingly, for a hydrosilylation involving unsaturated amine compounds, the precious metal catalysts known in the art are normally less effective in promoting a direct reaction between these unsaturated amine compounds with Si-hydride substrates, and will often lead to the formation of mixtures of undesired isomers.

Further, due to the high price of precious metals, the precious metal-containing catalysts can constitute a significant proportion of the cost of silicone formulations. Recently, global demand for precious metals, including platinum, has increased, driving prices for platinum to record highs, creating a need for effective, low cost replacement catalysts.

Silahydrocarbons contain only carbon, hydrogen and silicon atoms, and are useful in a variety of industrial applications. For example, tetraalkylsilanes, wherein two or more of the alkyl groups have between eight and twenty carbon atoms, have been shown to be useful and effective hydraulic fluids and lubricants, especially in aerospace and space vehicles. Pettigrew (*Synthetic Lubricants and High Performance Fluids (second edition)*, L. R. Rudnick and L. R. Shubkin (Editors), Marcel Dekker, NY 1999, PP 287-296) has reviewed various methods for synthesizing these fluids, many of which rely on hydrosilylation, catalyzed by precious metal catalysts (Rh, Pt, Pd) for hydrosilylation of alpha olefins by primary, secondary, and tertiary silanes. Specific disclosures of such syntheses using precious metal catalysts include the following:

U.S. Pat. No. 4,572,971 disclosed the rhodium-catalyzed hydrosilylation synthesis of saturated and unsaturated silahydrocarbons from alpha olefins and dialkylsilanes and/or trialkylsilanes. Completely saturated silahydrocarbon products were obtained by hydrogenation of the unsaturated silahydrocarbons byproducts.

U.S. Pat. No. 4,578,497 disclosed the platinum-catalyzed hydrosilylation of alpha olefins with primary ($—SiH_3$), secondary ($=SiH_2$) and tertiary ($\equiv SiH$) silanes to produce a reaction mixture still containing unreacted SiH functionality and subsequently introducing air or oxygen to complete the conversion to the tetraalkylsilane.

Lewis, et al., (*Organometallics* 9 (1990) 621-625) reported that both rhodium and platinum colloids catalyze the hydrosilylation synthesis of $CH_3(C_{10}H_{21})Si(C_8H_{17})_2$ from $CH_3(C_{10}H_{21})SiH_2$ and 1-octene. Rhodium was more active than platinum and injection of air or oxygen was critical to obtaining complete conversion of the starting materials to the silahydrocarbon. The primary ($—SiH_3$) and secondary silanes ($=SiH_2$) inhibited the platinum catalysis, but no inhibition was observed with rhodium.

LaPointe, et al., (*J. Amer. Chem. Soc.,* 119 (1997) 906-917) reported the palladium-catalyzed hydrosilylation synthesis of tetralkylsilanes from tertiary silanes and olefins.

Bart, et al (*J. Amer. Chem. Soc.,* 126 (2004) 13794-13807) reported that the bis(imino)pyridine iron di-nitrogen compound $(^{iPr}PDI)Fe(N_2)_2$ [$^{iPr}PDI=2,6-(2,6-(iPr)_2-C_6H_3N=CMe)_2C_5H_3N$] was an effective catalyst for hydrosilylation of alkenes and alkynes by primary and secondary silanes. However, the reaction products always had one or two SiH bonds and no tetraalkylsilanes were observed.

U.S. Pat. No. 8,236,915 discloses the use of manganese, iron, cobalt and nickel complexes of terdentate pyridine diimine ligands as hydrosilylation catalysts. However, this reference does not disclose use of these catalysts in the production of unsaturated silahydrocarbons.

Trisilahydrocarbon compounds are disclosed in U.S. Pat. No. 4,788,312. They are synthesized by a method comprising (1) Pt-catalyzed hydrosilylation of a large molar excess of alpha, omega dienes of four to sixteen carbon atoms by dihalosilanes to yield bis(alkenyl)dihalosilanes, and (2) further hydrosilylation of the bis(alkenyl)dihalosilanes by a trialkylsilane, or (3) further hydrosilylation of the bis(alkenyl)dihalosilanes by a trihalosilane and (4) substitution of the halogen atoms by reaction with Grignard, organolithium or organozinc reagents.

U.S. Pat. Nos. 5,026,893 and 6,278,011 disclose polysilahydrocarbons by methods comprising Pt-catalyzed hydrosilylation of substrates such as alkyltrivinylsilanes, phenyltrivinylsilane or trivinylcyclohexane with trialkylsilanes. The hydrosilylation methods disclosed are unreactive with internal olefins (See U.S. Pat. No. 6,278,011, Column 4, lines 2-6).

As an alternative to precious metals, recently, certain iron complexes have gained attention for use as hydrosilylation catalysts. Illustratively, technical journal articles have disclosed that that $Fe(CO)_5$ catalyzes hydrosilylation reactions at high temperatures. (Nesmeyanov, A. N. et al., Tetrahedron 1962, 17, 61), (Corey, J.Y et al., J. Chem. Rev. 1999, 99, 175), (C. Randolph, M. S. Wrighton, J. Am. Chem. Soc. 108 (1986) 3366). However, unwanted by-products such as the unsaturated silyl olefins, which result from dehydrogenative silylation, were formed as well.

A five-coordinate Fe(II) complex containing a pyridine di-imine (PDI) ligand with isopropyl substitution at the ortho positions of the aniline rings has been used to hydrosilylate an unsaturated hydrocarbon (1-hexene) with primary and secondary silanes such as $PhSiH_3$ or $Ph_2SiH_2$ (Bart et al., J. Am. Chem. Soc., 2004, 126, 13794) (Archer, A. M. et al. Organometallics 2006, 25, 4269). However, one of the limitations of these catalysts is that they are only effective in hydrosilylating the aforementioned primary and secondary phenyl-substituted silanes, and not in hydrosilylating tertiary or alkyl-substituted silanes such as $Et_3SiH$, or with alkoxy substituted silanes such as $(EtO)_3SiH$.

Other Fe-PDI complexes have also been disclosed. U.S. Pat. No. 5,955,555 discloses the synthesis of certain iron or cobalt PDI dianion complexes. The preferred anions are chloride, bromide and tetrafluoroborate. U.S. Pat. No. 7,442,819 discloses iron and cobalt complexes of certain tricyclic ligands containing a "pyridine" ring substituted with two imino groups. U.S. Pat. Nos. 6,461,994, 6,657,026 and 7,148,304 disclose several catalyst systems containing certain transitional metal-PDI complexes. U.S. Pat. No. 7,053,020 discloses a catalyst system containing, inter alia, one or more bisarylimino pyridine iron or cobalt catalyst. However, the catalysts and catalyst systems disclosed in these references are described for use in the context of olefin polymerizations and/or oligomerisations, not in the context of hydrosilylation reactions.

There is a continuing need in the hydrosilation industry for selectively catalyzing hydrosilylation reactions, particularly those involving silahydrocarbons such as tetraalkylsilanes from alkenes and primary and/or secondary silanes. A method of producing silahydrocarbons catalyzed by compounds of non-precious transition metals such as manganese, iron, cobalt and nickel, would be useful in the industry. The present invention provides one answer to that need.

SUMMARY OF THE INVENTION

In one aspect, the present invention is directed to a process for the production of silahydrocarbons, comprising: reacting at least one first reactant with at least one second reactant in the presence of a catalyst, to produce silahydrocarbons of general formulae $R^1R^2R^3R^4Si$, $R^1R^2R^3Si(Q)SiR^1R^2R^3$, $R^5R^6R^7R^8Si$, $R^5R^6R^7Si(Q)SiR^5R^7R^8$, $(R^1)_2Si[QSi(R^1)_3]_2$, $R^1Si[QSi(R^1)_3]_3$, or $Si[QSi(R^1)_3]_4$, wherein $R^1$, $R^2$, $R^3$, $R^4$, $R^5$, $R^6$, $R^7$, and $R^8$ are selected from the group consisting of aliphatic, aryl, alkaryl, aralkyl, and cycloaliphatic univalent hydrocarbyl groups having from one to thirty carbon atoms, with the proviso that at least one of $R^5$, $R^6$, $R^7$ or $R^8$ has an alkenyl functional group; and Q is a straight or branched alkylene group having from two to twenty carbon atoms;

wherein the first reactant comprises olefins of 2 to 30 carbon atoms and alkenylsilanes of general formulae $(R^1)_2Si(R^k)_2$, $(R^1)_3Si(R^k)_3$, or $Si(R^k)_4$ wherein $R^k$ is an alkenyl group of two to thirty carbons and $R^1$ is an aliphatic, aryl, alkaryl, aralkyl, and cycloaliphatic univalent hydrocarbyl groups having from one to thirty carbon atoms;

wherein the second reactant comprises monosilane ($SiH_4$) and hydridosilanes of general formulae, $R'SiH_3$, $(R')_2SiH_2$, or $(R')_3SiH$, or $(R')_nH_{3-n}SiQSi(R')_yH_{3-y}$ wherein n is 0, 1, 2, or 3, y is 0, 1, 2, or 3, n+y≥1, and R' is an aliphatic, aryl, alkaryl, aralkyl, and cycloaliphatic univalent hydrocarbyl group having from one to thirty carbon atoms such as methyl, ethyl, octyl, octadecyl, phenyl, tolyl, phenylethyl, mesityl and cyclohexylpropyl; and wherein the catalyst comprises iron complexes of terdentate pyridine diimine ligands of Formulae (I) or (II):

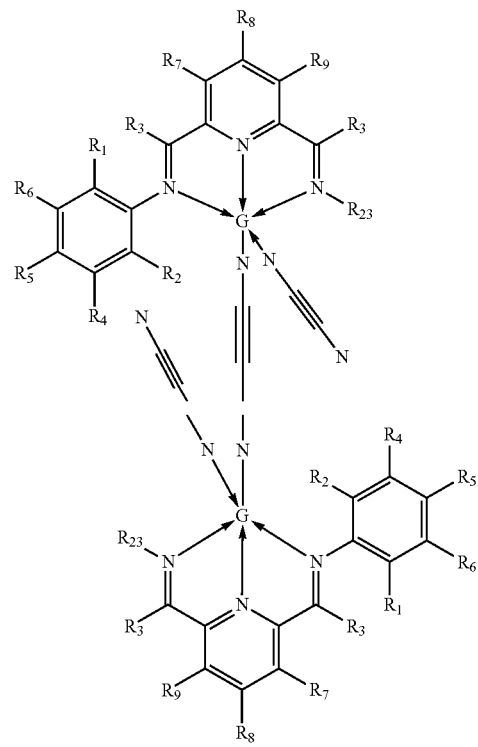

FORMULA (I)

-continued

FORMULA (II)

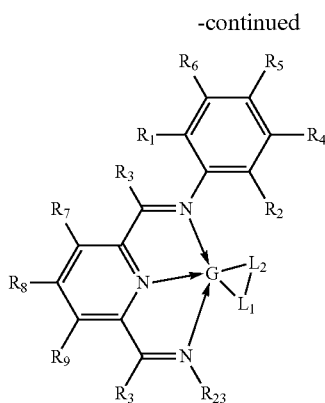

wherein:

G is Fe;

each occurrence of $R_1$, $R_2$, $R_3$, $R_4$, $R_5$, $R_6$, $R_7$, $R_8$, and $R_9$ is independently hydrogen, C1-C18 alkyl, C1-C18 substituted alkyl, aryl, substituted aryl, or an inert substituent, wherein $R_2$-$R_9$, other than hydrogen, optionally contain at least one heteroatom;

each occurrence of $R_{23}$ is independently C1-C18 alkyl, C1-C18 substituted alkyl, aryl or substituted aryl, wherein $R_{23}$ optionally contains at least one heteroatom; optionally, any two of $R_1$, $R_2$, $R_3$, $R_4$, $R_5$, $R_6$, $R_7$, $R_8$, $R_9$, and $R_{23}$ vicinal to one another taken together may form a ring being a substituted or unsubstituted, saturated, or unsaturated cyclic structure wherein $L_1$-$L_2$ is Formula (A)

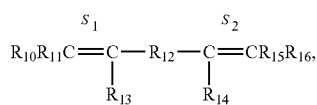

Formula (B)

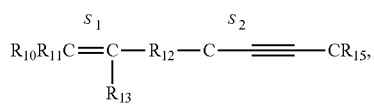

Formula (C)

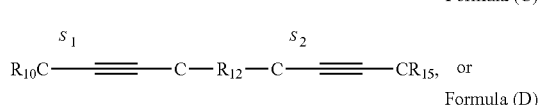

Formula (D)

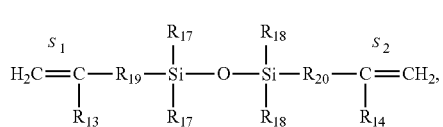

wherein each occurrence of $R_{10}$, $R_{11}$, $R_{13}$, $R_{14}$, $R_{15}$, and $R_{16}$ is independently hydrogen, C1-C18 alkyl, C2-C18 alkenyl, or C2-C18 alkynyl, wherein $R_{10}$, $R_{11}$, $R_{13}$, $R_{14}$, $R_{15}$, and $R_{16}$, other than hydrogen, optionally contain at least one heteroatom, and $R_{10}$, $R_{11}$, $R_{13}$, $R_{14}$, $R_{15}$, and $R_{16}$, other than hydrogen, are optionally substituted, each occurrence of $R_{12}$ is independently C1-C18 alkylene, C1-C18 substituted alkylene, C2-C18 alkenylene, C2-C18 substituted alkenylene, C2-C18 alkynylene, C2-C18 substituted alkynylene, arylene, or a substituted arylene, wherein $R_{12}$ optionally contains at least one heteroatom;

optionally any two of $R_{10}$, $R_{11}$, $R_{12}$, $R_{13}$, $R_{14}$, $R_{15}$, and $R_{16}$ taken together form a ring being a substituted or unsubstituted, saturated or unsaturated cyclic structure;

each occurrence of $R_{17}$ and $R_{18}$ is independently alkyl, substituted alkyl, aryl, or substituted aryl, wherein each of $R_{17}$ and $R_{18}$ optionally contains at least one heteroatom, and wherein $R_{17}$ and $R_{18}$ taken together optionally form a ring being a substituted or unsubstituted, saturated or unsaturated cyclic structure;

each occurrence of $R_{19}$ and $R_{20}$ is independently a covalent bond that connects Si and C, an alkylene, substituted alkylene, or a heteroatom, wherein $R_{19}$ and $R_{20}$ optionally contain at least one heteroatom;

wherein $L_1$-$L_2$ bonds with G through unsaturated sites $S_1$ and $S_2$;

with the provisos that (1) $R_1$ in Formula (I) is hydrogen, methyl, ethyl or n-propyl; and (2) $L_1$-$L_2$ of Formula (A) is selected from the group consisting of 1,3-divinyltetramethyldisiloxane, 1,3-butadiene, 1,5-cyclooctadienes, dicyclopentadienes, and norbornadienes.

In another aspect, the present invention is directed to a process for hydrosilylation/dehydrogenative silylation synthesis comprising reacting C2-C30 olefins and primary silanes of general formula $R'SiH_3$ or monosilane $(SiH_4)$ in the presence of the catalyst of Formula (III)

Formula (III)

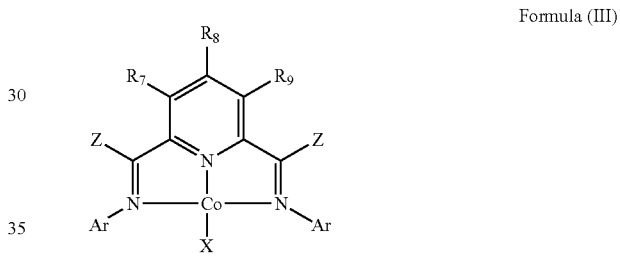

wherein:

each occurrence of Ar is independently C1-C18 alkyl, C1-C18 substituted alkyl, aryl, or substituted aryl, wherein Ar optionally contains at least one heteroatom;

Z is independently hydrogen, C1-C18 alkyl, C1-C18 substituted alkyl, aryl, substituted aryl, or an inert functional group;

$R_7$, $R_8$ and $R_9$ are independently hydrogen, C1-C18 alkyl, C1-C18 substituted alkyl, aryl, substituted aryl, or an inert functional group;

X is $N_2$, CO, alkyl, OH, SH, SeH, —H, or $SiR_3$ where R is an alkyl, aryl, or siloxanyl group;

to produce alkylbis(alkenyl)-silanes and arylbis(alkenyl) silanes of formula $R^1(R^k)_2SiH$, alkenylbis(alkyl)silanes and arylalkenylalkylsilanes of formula $(R^1)_2R^kSiH$, or tetralkenylsilanes of general formula $Si(R^k)_4$, wherein $R^1$ is an aliphatic, aryl, alkaryl, aralkyl, and cycloaliphatic univalent hydrocarbyl groups having from one to thirty carbon atoms; R' is an aliphatic, aryl, alkaryl, aralkyl, and cycloalpihatic univalent hydrocarbyl group having from one to thirty carbon atoms such as methyl, ethyl, octyl, octadecyl, phenyl, tolyl, phenylethyl, mesityl, and cyclohexylpropyl; and $R^k$ is an alkenyl group of two to thirty carbons.

DETAILED DESCRIPTION OF THE INVENTION

As defined herein, silahydrocarbons contain only carbon, hydrogen, and silicon atoms. Saturated silahydrocarbons have general formulae such as, $R^1R^2R^3R^4Si$ or $R^1R^2R^3Si(Q)SiR^1R^2R^3$, wherein $R^1$, $R^2$, $R^3$, $R^4$ are aliphatic, aryl, alkaryl, aralkyl, and cycloaliphatic univalent hydrocarbyl groups having from one to thirty carbon atoms such as methyl, ethyl, octyl, octadecyl, phenyl, phenylethyl, and cyclohexylpropyl.

Polysilahydrocarbon compounds contain more than one silicon atom per molecule. Q is a bridging group between silicon atoms in polysilahydrocarbons. Thus, Q can be a straight-chained or branched alkylene group having from two to twenty carbon atoms.

Unsaturated silahydrocarbons have general formulae such as, $R^5R^6R^7R^8Si$ or $R^5R^6R^7Si(O)SiR^5R^7R^8$ in which at least one of the R groups ($R^5$-$R^8$) has an alkenyl (—C=C—) functionality such as vinyl, allyl or propenyl. Q has the same meaning as defined above.

The alkyl alkenylsilanes and phenyl alkenylsilanes of this invention are defined as $R'SiHR_2$, $R'_2SiHR$, or $R'SiH_2R$, wherein R' is an aliphatic, aryl, alkaryl, alkylene, and cycloaliphatic univalent hydrocarbyl group having from one to thirty carbon atoms such as methyl, ethyl, octyl, octadecyl, phenyl, tolyl, phenylethyl, mesityl, and cyclohexylpropyl. R is a univalent hydrocarbyl group of three to thirty carbon atoms with one carbon double bond (—C=C—) in the chain.

Hydrosilylation is the addition of an SiH functionality to an unsaturated group such as an alkene, alkyne, ketone, or nitrile. Hydrosilylation of an alkene results in the formation of a saturated product. When the SiH addition to the alkene results in the formation of an unsaturated product, such as a vinylsilane or allylsilane, and hydrogen and/or a hydrogenated co-product, such as an alkane, then the process is called Dehydrogenative Silylation. Both hydrosilylation and dehydrogenative silylation can occur simultaneously in the same reaction.

As used in the instant application, "alkyl" includes straight, branched and cyclic alkyl groups. Specific and non-limiting examples of alkyls include, but are not limited to, methyl, ethyl, propyl, hexyl, octyl, and isobutyl. In some embodiments, the alkyl group is a C1-C18 alkyl. In other embodiments, it is a C1-C10 alkyl or C1-C30 alkyl.

By "substituted alkyl" herein is meant an alkyl group that contains one or more substituent groups that are inert under the process conditions to which the compound containing these groups is subjected. The substituent groups also do not substantially interfere with the hydrosilylation and dehydrogenative silylation processes described herein. In some embodiments, the substituted alkyl group is a C1-C18 substituted alkyl. In other embodiments, it is a C1-C10 substituted alkyl. The substituents for the alkyl include, but are not limited to, the inert functional groups described herein.

By "aryl" herein is meant a non-limiting group of any aromatic hydrocarbon from which one hydrogen atom has been removed. An aryl may have one or more aromatic rings, which may be fused, connected by single bonds or other groups. Specific and non-limiting examples of aryls include, but are not limited to, tolyl, xylyl, phenyl, and naphthalenyl.

By "substituted aryl" herein is meant an aromatic group that contains one or more substituent groups that are inert under the process conditions to which the compound containing these substituent groups is subjected. The substituent groups also do not substantially interfere with the hydrosilylation and dehydrogenative processes described herein. Similar to an aryl, a substituted aryl may have one or more aromatic rings, which may be fused, connected by single bonds or other groups; however, when the substituted aryl has a heteroaromatic ring, the free valence in the substituted aryl group can be to a heteroatom (such as nitrogen) of the heteroaromatic ring instead of a carbon. If not otherwise stated, it is preferred that the substituents of the substituted aryl groups herein contain 0 to about 30 carbon atoms, specifically from 0 to 20 carbon atoms, more specifically, from 0 to 10 carbon atoms. In one embodiment, the substituents are the inert groups described herein.

By "alkenyl" herein is meant any straight, branched, or cyclic alkenyl group containing one or more carbon-carbon double bonds, where the point of substitution can be either at a carbon-carbon double bond or elsewhere in the group. Specific and non-limiting examples of alkenyls include, but are not limited to, vinyl, propenyl, allyl, methallyl, and ethylidenyl norbornane.

By "aralkyl" herein is meant an alkyl group in which one or more hydrogen atoms have been substituted by the same number of aryl groups, which aryl groups may be the same or different from one another. Non-limiting examples of aralkyls include benzyl and phenylethyl.

As indicated above, the present invention is a process for the production of silahydrocarbons of general formulae $R^1R^2R^3R^4Si$, $R^1R^2R^3Si(Q)SiR^1R^2R^3$, $R^5R^6R^7R^8Si$, $R^5R^6R^7Si(O)SiR^5R^7R^8$ $(R^1)_2Si[QSi(R^1)_3]_2$, $R^1Si[QSi(R^1)_3]_3$ or $Si[QSi(R^1)_3]_4$ wherein $R^1$, $R^2$, $R^3$, $R^4$, $R^5$, $R^6$, $R^7$, and $R^8$ are aliphatic, aryl, alkaryl, aralkyl, and cycloaliphatic univalent hydrocarbyl groups having from one to thirty carbon atoms (methyl, ethyl, octyl, octadecyl, phenyl, phenylethyl, cyclohexylpropyl and the like), with the proviso that at least one of the R groups ($R^5$-$R^8$) has an alkenyl (—C=C—) functional group; Q is a straight or branched alkylene group having from two to twenty carbon atoms bridging the silicon atoms in silahydrocarbons having more than one silicon atom. The process of the invention comprises reacting at least one olefin or alkenylsilane with a monosilane or hydridosilane in the presence of iron complexes of terdentate pyridine diimine ligands as depicted in Formulae (I) or (II):

FORMULA (I)

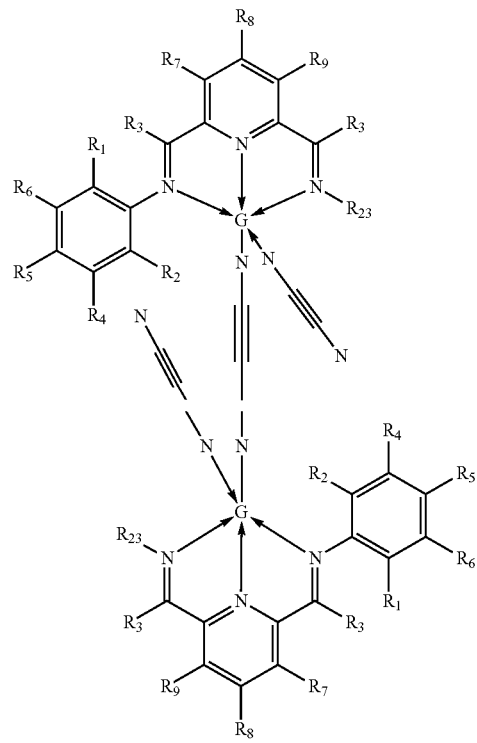

-continued

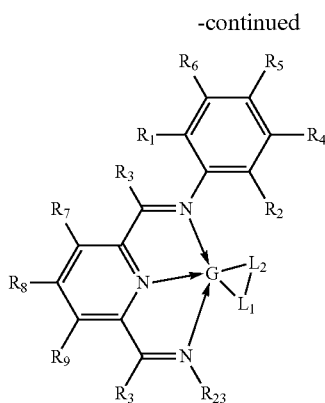

FORMULA (II)

In Formulae (I) and (II), G is Fe; each occurrence of $R_1$, $R_2$, $R_3$, $R_4$, $R_5$, $R_6$, $R_7$, $R_8$, and $R_9$ is independently hydrogen, C1-C18 alkyl, C1-C18 substituted alkyl, aryl, substituted aryl, or an inert functional group, wherein $R_2$-$R_9$, other than hydrogen, optionally contain at least one heteroatom;

each occurrence of $R_{23}$ is independently C1-C18 alkyl, C1-C18 substituted alkyl, aryl, or substituted aryl, wherein $R_{23}$ optionally contains at least one heteroatom; optionally, any two of $R_1$, $R_2$, $R_3$, $R_4$, $R_5$, $R_6$, $R_7$, $R_8$, $R_9$, and $R_{23}$ vicinal to one another taken together may form a ring being a substituted or unsubstituted, saturated, or unsaturated cyclic structure wherein $L_1$-$L_2$ is

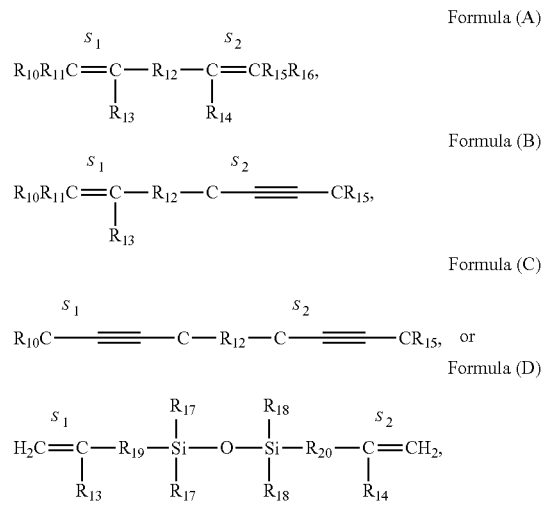

wherein each occurrence of $R_{10}$, $R_{11}$, $R_{13}$, $R_{14}$, $R_{15}$ and $R_{16}$ is independently hydrogen, C1-C18 alkyl, C2-C18 alkenyl, or C2-C18 alkynyl, wherein $R_{10}$, $R_{11}$, $R_{13}$, $R_{14}$, $R_{15}$ and $R_{16}$, other than hydrogen, optionally contain at least one heteroatom, and $R_{10}$, $R_{11}$, $R_{13}$, $R_{14}$, $R_{15}$ and $R_{16}$, other than hydrogen, are optionally substituted, each occurrence of $R_{12}$ is independently C1-C18 alkylene, C1-C18 substituted alkylene, C2-C18 alkenylene, C2-C18 substituted alkenylene, C2-C18 alkynylene, C2-C18 substituted alkynylene, arylene, or substituted arylene, wherein $R_{12}$ optionally contains at least one heteroatom;

optionally any two of $R_{10}$, $R_{11}$, $R_{12}$, $R_{13}$, $R_{14}$, $R_{15}$, $R_{16}$ taken together form a ring being a substituted or unsubstituted, saturated or unsaturated cyclic structure;

each occurrence of $R_{17}$ and $R_{18}$ is independently alkyl, substituted alkyl, aryl, or substituted aryl, wherein each of $R_{17}$ and $R_{18}$ optionally contains at least one heteroatom, and wherein $R_{17}$ and $R_{18}$ taken together optionally form a ring being a substituted or unsubstituted, saturated or unsaturated cyclic structure;

each occurrence of $R_{19}$ and $R_{20}$ is independently a covalent bond that connects Si and C, an alkylene, substituted alkylene, or a heteroatom, wherein $R_{19}$ and $R_{20}$ optionally contain at least one heteroatom;

wherein $L_1$-$L_2$ bonds with G through unsaturated sites $S_1$ and $S_2$;

with the provisos that (1) $R_1$ in Formula (I) is hydrogen, methyl, ethyl or n-propyl; and (2) $L_1$-$L_2$ of Formula (A) is selected from the group consisting of 1,3-divinyltetramethyldisiloxane, 1,3-butadiene, 1,5-cyclooctadienes, dicyclopentadienes, and norbornadienes.

Preferably, the reacting olefin or alkenylsilane include olefins of 2 to 30 carbon atoms and alkenylsilanes of general formulae $(R^1)_2Si(R^k)_2$, $(R^1)_3Si(R^k)$, $(R^1)Si(R^k)_3$, or $Si(R^k)_4$ wherein $R^k$ is an alkenyl group of two to thirty carbons Preferably, the monosilane or hydridosilane include monosilane ($SiH_4$) and hydridosilanes of general formulae, $R'SiH_3$, $(R')_2SiH_2$, $(R')_3SiH$, or $(R')_nH_{3-n}SiQSi(R')_yH_{3-y}$ wherein n is 0, 1, 2, or 3, y is 0, 1, 2, or 3, n+y≥1, and R' is an aliphatic, aryl, alkaryl, and cycloaliphatic univalent hydrocarbyl group having from one to thirty carbon atoms such as methyl, ethyl, octyl, octadecyl, phenyl, tolyl, phenylethyl, mesityl, and cyclohexylpropyl.

In one preferred embodiment, the present invention is a catalytic hydrosilylation process for synthesizing silahydrocarbons of general formula $R^1R^2R^3R^4Si$, from primary silanes of general formula $R'SiH_3$, secondary silanes of general formula $(R')_2SiH_2$, or tertiary silanes of general formula $(R')_3SiH$, and C2-C30 olefins, characterized by the use iron complexes of terdentate pyridine diimine ligands according to Formula (I) or Formula (II). In the silahydrocarbon formula, $R^1$, $R^2$, $R^3$, $R^4$ are aliphatic, aryl, alkaryl, aralkyl, and cycloaliphatic univalent hydrocarbyl groups having from one to thirty carbon atoms such as methyl, ethyl, octyl, octadecyl, phenyl, phenylethyl and cyclohexylpropyl. R' is an aliphatic, aryl, alkaryl, and cycloaliphatic univalent hydrocarbyl group having from one to thirty carbon atoms such as methyl, ethyl, octyl, octadecyl, phenyl, tolyl, phenylethyl, mesityl, and cyclohexylpropyl. The R' radicals are not all the same in the general formulae of the secondary and tertiary silanes. Unsaturation in the C2-C30 olefins can be terminal or internal.

In Formula (I) and Formula (II), G is Fe; each occurrence of $R_1$, $R_2$, $R_3$, $R_4$, $R_5$, $R_6$, $R_7$, $R_8$, and $R_9$ is independently hydrogen, C1-C18 alkyl, C1-C18 substituted alkyl, aryl, substituted aryl, or an inert functional group, wherein $R_2$-$R_9$, other than hydrogen, optionally contain at least one heteroatom; each occurrence of $R_{23}$ is independently C1-C18 alkyl, C1-C18 substituted alkyl, aryl or substituted aryl, wherein $R_{23}$ optionally contains at least one heteroatom. Optionally, any two of $R_1$, $R_2$, $R_3$, $R_4$, $R_5$, $R_6$, $R_7$, $R_8$, $R_9$, and $R_{23}$ vicinal to one another taken together may form a ring being a substituted or unsubstituted, saturated, or unsaturated cyclic structure.

FORMULA (I)

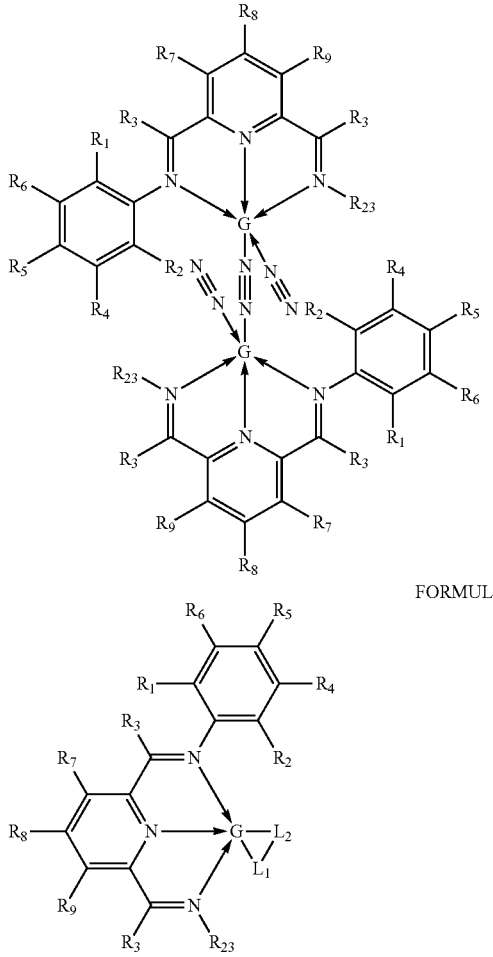

FORMULA (II)

$L_1$-$L_2$ is

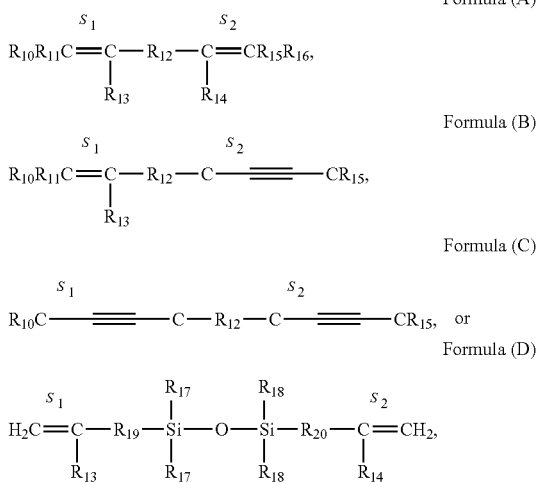

Formula (A)

Formula (B)

Formula (C)

Formula (D)

wherein each occurrence of $R_{10}$, $R_{11}$, $R_{13}$, $R_{14}$, $R_{15}$ and $R_{16}$ is independently hydrogen, C1-C18 alkyl, C2-C18 alkenyl, or C2-C18 alkynyl, wherein $R_{10}$, $R_{11}$, $R_{13}$, $R_{14}$, $R_{15}$ and $R_{16}$, other than hydrogen, optionally contain at least one heteroatom, and $R_{10}$, $R_{11}$, $R_{13}$, $R_{14}$, $R_{15}$ and $R_{16}$, other than hydrogen, are optionally substituted;

each occurrence of $R_{12}$ is independently C1-C18 alkylene, C1-C18 substituted alkylene, C2-C18 alkenylene, C2-C18 substituted alkenylene, C2-C18 alkynylene, C2-C18 substituted alkynylene, arylene, substituted arylene, wherein $R_{12}$ optionally contains at least one heteroatom;

optionally any two of $R_{10}$, $R_{11}$, $R_{12}$, $R_{13}$, $R_{14}$, $R_{15}$, $R_{16}$ taken together form a ring being a substituted or unsubstituted, saturated or unsaturated cyclic structure;

each occurrence of $R_{17}$ and $R_{18}$ is independently alkyl, substituted alkyl, aryl, or substituted aryl, wherein each of $R_{17}$ and $R_{18}$ optionally contains at least one heteroatom, and wherein $R_{17}$ and $R_{18}$ taken together optionally form a ring being a substituted or unsubstituted, saturated or unsaturated cyclic structure;

each occurrence of $R_{19}$ and $R_{20}$ is independently a covalent bond that connects Si and C, an alkylene, substituted alkylene, or a heteroatom, wherein $R_{19}$ and $R_{20}$ optionally contain at least one heteroatom;

wherein $L_1$-$L_2$ bonds with G through unsaturated sites $S_1$ and $S_2$;

with the proviso that (1) $R_1$ in Formula (I) is hydrogen, methyl, ethyl or n-propyl; and (2) $L_1$-$L_2$ of Formula (A) is selected from the group consisting of 1,3-divinyltetramethyldisiloxane, 1,3-butadiene, 1,5-cyclooctadienes, dicyclopentadienes, and norbornadienes.

In a second preferred embodiment, cobalt-containing compounds of Formula (III) are used in the hydrosilylation/dehydrogenative silylation synthesis of alkylbis(alkenyl)-silanes and arylbis(alkenyl)silanes of formula $R^1(R^k)_2SiH$, alkenylbis(alkyl)silanes and arylalkenylalkylsilanes of formula $(R^1)_2R^kSiH$, and tetralkenylsilanes of general formula $Si(R^k)_4$ from C2-C30 olefins and primary silanes of general formula, $R'SiH_3$ or monosilane ($SiH_4$). $R^1$ and $R'$ have the same meanings as hereinabove defined. $R^k$ is an alkenyl group of two to thirty carbons.

Formula (III)

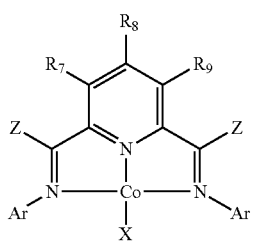

In Formula (III), each occurrence of Ar is independently C1-C18 alkyl, C1-C18 substituted alkyl, aryl or substituted aryl, wherein Ar optionally contains at least one heteroatom. Z is independently hydrogen, C1-C18 alkyl, C1-C18 substituted alkyl, aryl, substituted aryl, or an inert substituent. Z can optionally contain at least one heteroatom. $R_7$, $R_8$, and $R_9$ have the same meanings as defined hereinabove in Formula (I). X can be $N_2$, CO, alkyl such as methyl, OH, SH, SeH, —H, or $SiR_3$ where R is an alkyl, aryl, or siloxanyl group.

In a third preferred embodiment, iron-containing compounds of Formula (I) or Formula (II) are used in the hydrosilylation synthesis of saturated and unsaturated silahydrocarbons from alkylbis(alkenyl)silanes and arylbis(alkenyl) silanes of formula $R^1(R^k)_2SiH$, and alkenylbis(alkyl)silanes and arylalkenylalkylsilanes of formula $(R^1)_2R^k$SiH with C2-C30 olefins. The formulae of products of these hydrosilylation reactions are $(R^1)_2(R^k)_2$Si and $(R^1)_3R^k$Si, respectively.

In a fourth preferred embodiment, the synthesis of saturated and unsaturated silahydrocarbons having more than one silicon atom per molecule is done by reacting unsaturated compounds of formulae $(R^1)_2$Si$(R^k)_2$ and/or $(R^1)_3$Si$(R^k)$ and/or $(R^1)$Si$(R^k)_3$ and/or Si$(R^k)_4$ with hydridosilanes of formulae $(R^1)_3$SiH and/or $(R^1)(R^k)_2$SiH and/or $(R^1)_2(R^k)$SiH in the presence of pyridine diimine complexes of Formulae (I), (II), or (III). The saturated silahydrocarbon products containing more than one silicon atom per molecule derived from $(R^1)_3$SiH in this embodiment have general formulae, $(R^1)_3$SiQSi$(R^1)_3$, $(R^1)_2$Si$[QSi(R^1)_3]_2$, $R^1$Si$[QSi(R^1)_3]_3$ and Si$[QSi(R^1)_3]_4$. As was defined hereinabove, Q is a straight-chained or branched alkylene group having from two to twenty carbon atoms. Saturated polysilahydrocarbons can also be synthesized by hydrosilylation of olefins with hydrides of general formula, $(R')_{3-n}H_n$SiQSi$(R')_{3-y}H_y$ (n=0, 1, 2, 3; y=0, 1, 2, 3; n+y≥1) in the presence of the aforementioned pyridine diimine complexes. Unsaturated polysilahydrocarbons are formed in the hydrosilylation/dehydrogenative silylation reactions of $(R^1)_n$Si$(R^k)_4$, (n=1, 2, 3) and $(R^1)_m(R^k)_{3-m}$SiH (m=1, 2) as well as in the autoreactions of $(R^1)_m(R^k)_{3-m}$SiH (m=1, 2).

The present invention discloses the synthesis via hydrosilylation of silahydrocarbons (also known as tetraalkylsilanes) of general formula, $R^1R^2R^3R^4$Si. $R^1$, $R^2$, $R^3$, $R^4$ are aliphatic, aryl, alkaryl, aralkyl, and cycloaliphatic univalent hydrocarbyl groups having from one to thirty carbon atoms such as methyl, ethyl, octyl, octadecyl, phenyl, phenylethyl and cyclohexylpropyl. Examples of these silahydrocarbons are methyltri(octyl)silane, dimethyl(dioctyl)silane, methyl (hexyl)(decyl)octadecylsilane, tetra(octyl)silane, phenyltri (octyl)silane, phenyl(dipentyl)dodecylsilane and phenyl(dinonyl)butylsilane.

The compounds are synthesized by hydrosilylation of C2-C30 olefins with monosilane (SiH$_4$), primary silanes of general formula R'SiH$_3$, secondary silanes of general formula $(R')_2$SiH$_2$, tertiary silanes of general formula $(R')_3$SiH, or combinations thereof. R' is an aliphatic, aryl, alkaryl, aralkyl, and cycloaliphatic univalent hydrocarbyl group having from one to thirty carbon atoms such as methyl, ethyl, octyl, octadecyl, phenyl, tolyl, phenylethyl, mesityl and cyclohexylpropyl. The R' radicals are not all the same in the general formulae of the secondary and tertiary silanes. Examples of primary silanes are methylsilane, butylsilane, amylsilane, hexylsilane, octylsilane, phenylsilane, phenyethylsilane, octadecylsilane, cyclohexylsilane and mixtures thereof. Suitable secondary silanes are dimethylsilane, methyl(decyl)silane, ethyl (nonyl)silane, phenyl(phenethyl)silane, dioctylsilane, hexyltetradecylsilane and combinations thereof. Examples of tertiary silanes are trioctylsilane, methyl(diheptyl)silane, butyl(nonyl)dodecylsilane, phenyl(dioctyl)silane, tri(dodecyl)silane and mixtures thereof.

It is not necessary that the C2-C30 olefins be individually pure compounds, or that the unsaturation be terminal. Mixtures of olefins, including those with internal unsaturation, are suitable for the hydrosilylation synthesis of the instant invention. Thus, suitable examples include all the positional and geometric isomers of butene, pentene, hexene, octene, nonene, dodecene, tetradecene, triacontene and their mixtures. The iron pyridine diimine catalysts of this invention, depicted in Formula (I) and Formula (II), can effect the hydrosilylation of olefins with internal carbon-carbon double bonds.

In Formula (I) and Formula (II), G is Fe; each occurrence of $R_1$, $R_2$, $R_3$, $R_4$, $R_5$, $R_6$, $R_7$, $R_8$, and $R_9$ is independently hydrogen, C1-C18 alkyl, C1-C18 substituted alkyl, aryl, substituted aryl, or an inert substituent, wherein $R_2$-$R_9$, other than hydrogen, optionally contain at least one heteroatom; each occurrence of $R_{23}$ is independently C1-C18 alkyl, C1-C18 substituted alkyl, aryl or substituted aryl, wherein $R_{23}$ optionally contains at least one heteroatom. Optionally, any two of $R_1$, $R_2$, $R_3$, $R_4$, $R_5$, $R_6$, $R_7$, $R_8$, $R_9$ and $R_{23}$ vicinal to one another taken together may form a ring being a substituted or unsubstituted, saturated, or unsaturated cyclic structure.

Preferred compositions of Formula (I) include $[(^{2,6-(R'')}PDI)Fe(N_2)]_2(\mu_2-N_2)$, PDI=2,6-(2,6-(R'')$_2$—C$_6$H$_3$N=CMe)$_2$C$_5$H$_3$N; R" is independently Me, Et, and Mesityl and PDI=2,6-(2,6-(R'')$_2$—C$_6$H$_3$N=CPhenyl)$_2$ C$_5$H$_3$N; R" is independently Me, Et, and Mesityl. It will be appreciated that R" represents $R_1$ and/or $R_2$ in Formula (I).

Preferred compositions of Formula (II) include $[(^{2,6-(R'')2}PDI)Fe(M^{vi}M^{vi})]$, PDI=2,6-(2,6-(R'')$_2$—C$_6$H$_3$N=CMe)$_2$C$_5$H$_3$N; R" is independently Me, Et, and Mesityl, $M^{vi}M^{vi}$=1, 3-Divinyltetramethyldisiloxane, $[(^{2,6-(R'')2}PDI)Fe(H_2C=CHCH=CH_2)]$, and PDI=2,6-(2,6-(R'')$_2$—C$_6$H$_3$N=CPhenyl)$_2$C$_5$H$_3$N; R" is independently Me, Et, and Mesityl It will be appreciated that R" represents $R_1$ and/or $R_2$ in Formula (II).

The iron-containing compounds of Formula (I) and Formula (II) are also effective for the hydrosilylation of C2-C30 olefins by alkylbis(alkenyl)silanes and arylbis(alkenyl)silanes of general formula, $R^1(R^k)_2$SiH, and alkenylbis(alkyl) silanes and arylalkenylalkylsilanes of general formula $(R^1)_2R^k$SiH, and their mixtures, to yield saturated and unsaturated silahydrocarbons. Additionally, they are effective for the hydrosilylation of C2-C30 olefins by $(R')_{3-n}H_n$SiQSi$(R')_{3-y}H_y$ (n=0, 1, 2, 3; y=0, 1, 2, 3; n+y≥1) to yield polysilahydrocarbons.

In $R^1(R^k)_2$SiH and $(R^1)_2R^k$SiH, $R^1$ and R' have the same meanings as hereinabove defined. $R^k$ is an alkenyl group of three to thirty carbons. The unsaturation in $R^k$ can be at any position along the carbon chain. Suitable examples of $R^1(R^k)_2$SiH include all isomers of methylbis(octenyl)silane, octylbis (butenyl)silane, decylbis(nonenyl)silane, methylbis(tetradecenyl)silane, phenylbis(octenyl)silane, phenylbis(dodecenyl)silane, octylbis(octenyl)silane, phenyl(octenyl) decenylsilane and their mixtures.

The unsaturated silahydrocarbon products of the hydrosilylation of the C2-C30 olefins by $R^1(R^k)_2$SiH have the general formula $(R^1)_2(R^k)_2$Si. Examples are dimethyldi(decenyl)silane, dioctlyldi(tetradecenyl)silane, methyl(octyl)di-(hexenyl)silane, phenyl(nonyl)di(dodecenyl)silane, octyl(decyl) (octenyl)-(decenyl)silane and phenyl(heptyl)(nonenyl) (undecenyl)silane.

Suitable examples of $(R^1)_2R^k$SiH include all isomers of dimethyl(tetradecenyl)-silane, didodecyl(decenyl)silane, diethyl(octenyl)silane, propyl(decyl)(heptenyl)-silane, phenyl(decyl)(nonenyl)silane, phenyl(tetradecyl)(dodecenyl)silane and mixtures thereof.

The unsaturated silahydrocarbon products of the hydrosilylation of the C2-C30 olefins by $(R^1)_2R^k$SiH have the general formula $(R^1)_3(R^k)$Si. Examples are tri(octyl)(hexadecenyl) silane, cyclohexyl(phenethyl)(heptyl)(nonenyl)silane, methyl(hexyl)(decyl)(dodecenyl)silane and ethyldi(pentyl)(tetradecenyl)silane.

Compounds of general formulae $R^1(R^k)_2$SiH and $(R^1)_2R^k$SiH are synthesized via hydrosilylation/dehydrogenative silylation of C2-C30 olefins by primary silanes, R'SiH$_3$ (already defined hereinabove), with cobalt pyridine diimine complexes of Formula (III) as catalysts. The corresponding C2-C30 alkane is a coproduct of the dehydrogenative silylation.

Suitable examples of the catalysts of Formula (III) include ($^{Mes}$PDICoCH$_3$) in which R$_7$-R$_9$ and Z are hydrogen, Ar is mestiyl and X is CH$_3$; ($^{Mes}$PDIMeCoCH$_3$) in which R$_7$-R$_9$ are hydrogen, Z is methyl, Ar is mestiyl and X is CH$_3$; ($^{2,6-iPr}$PDICoN$_2$) in which R$_7$-R$_9$ and Z are hydrogen, Ar is 2,6-diisopropyl-phenyl and X is N$_2$; ($^{2,6-iPr}$PDIMeCoN$_2$) in which R$_7$-R$_9$ are hydrogen, Z is methyl, Ar is 2,6-diisopropylphenyl and X is N$_2$; ($^{2,6-iPr}$PDIPhCON$_2$) in which R$_7$-R$_9$ are hydrogen, Z is phenyl, Ar is 2,6-diisopropylphenyl and X is N$_2$; ($^{2,6-iPr}$PDIMeCoOH) in which R$_7$-R$_9$ are hydrogen, Z is methyl, Ar is 2,6-diisopropylphenyl and X is OH; ($^{Mes}$PDI) CoOH in which R$_7$-R$_9$ and Z are hydrogen, Ar is mestiyl and X is OH; ($^{Mes}$PDI)CoCl in which R$_7$-R$_9$ and Z are hydrogen, Ar is mestiyl and X is Cl; ($^{2,6-Et}$PDI)CoN$_2$ in which R$_7$-R$_9$ and Z are hydrogen, Ar is 2,6-diethylphenyl and X is N$_2$; and ($^{2,6-iPr}$BPDI)CoN$_2$ in which R$_7$-R$_9$ are hydrogen, Z is isopropyl, Ar is mestiyl and X is N$_2$.

Silahydrocarbons with two silicon atoms per molecule are synthesized via the hydrosilylation of (R$^1$)$_3$(R$^k$)Si compounds by (R$^1$)$_3$SiH. Alternatively, they are synthesized via the hydrosilylation of C2-C30 olefins by the bissilyl hydrides, (R')$_{3-n}$H$_n$SiQSi(R')$_{3-y}$H$_y$ (n=0, 1, 2, 3; y=0, 1, 2, 3; n+y≥1). Those with three silicon atom per molecule are synthesized via the hydrosilylation of the compounds of general formula (R$^1$)$_2$Si(R$^k$)$_2$ by those of general formula, (R$^1$)$_3$SiH. Iron catalysts of Formula (I) or Formula (II) are employed in both cases.

The hydrosilylation and dehydrogenative silylation process of the present invention can be done with or without a solvent, but is advantageously done solventless. Hydrocarbon solvents such as hexane, cyclohexane, benzene, toluene and xylene can be used.

In general, stoichiometric amounts of olefin and hydridosilane will enable complete conversion of both functionalities to produce the desired product. However, there are instances in which a stoichiometric excess of olefin is preferred, for example in the synthesis of unsaturated silahydrocarbons from bis(alkenyl)silanes and olefins.

Effective catalyst usage for hydrosilylation and dehydrogenative silylation ranges from 0.01 mole percent to 10 mole percent based on the molar quantity of the alkene to be reacted. Preferred levels are from 0.1 to 5 mole percent. In still another embodiment, the catalyst level is from 0.2 mole percent to 1 mole percent. Reaction may be run at temperatures from about 0° C. up to 300° C., depending on the thermal stability of the alkene, silyl hydride and the specific pyridine diimine complex. Temperatures in the range, 20-100° C., have been found to effective for most reactions. Selectivity to dehydrogenative silylation is more pronounced at the lower temperatures of this range. Heating of reaction mixtures can be done using conventional methods as well as with microwave devices.

The hydrosilylation and dehydrogenative silylation reactions of this invention can be run at sub-atmospheric and supra-atmospheric pressures. Typically, pressures from about 1 atmosphere (0.1 MPa) to about 50 atmospheres (5.1 MPa) are suitable. Higher pressures are effective with volatile and/or less reactive alkenes which require confinement to enable high conversions.

A variety of reactors can be used in the process of this invention. Selection is determined by factors such as the volatility of the reagents and products. Continuously stirred batch reactors are conveniently used when the reagents are liquid at ambient and reaction temperature. With gaseous olefins, fixed-bed reactors and autoclave reactors can be more suitable.

The following examples are intended to illustrate, but in no way limit the scope of the present invention. All parts and percentages are by weight and all temperatures are in degrees Celsius unless explicitly stated otherwise. All the publications and the US patents referred to in the application are hereby incorporated by reference in their entireties.

EXAMPLES

General Considerations

All air- and moisture-sensitive manipulations were carried out using standard vacuum line, Schlenk, and cannula techniques or in an MBraun inert atmosphere dry box containing an atmosphere of purified nitrogen. Solvents for air- and moisture-sensitive manipulations were initially dried and deoxygenated using literature procedures (Pangborn, A B et al., *Organometallics* 15:1518 (1996)). Chloroform-d and benzene-d$_6$ were purchased from Cambridge Isotope Laboratories.

Synthesis of [($^{2,6-Et2}$PDI)Fe(N$_2$)]$_2$[μ-(N$_2$)], [($^{2,6-Me2}$PDI) Fe(N$_2$)]$_2$-[μ-(N$_2$)], [($^{2-Me,6-iPr}$PDI)Fe(N$_2$)]$_2$[μ-(N$_2$)], [$^{2,4,6-Me3}$PDIFe(N$_2$)]$_2$[μ-N$_2$] and [$^{2,6-iPr2}$PDIFe(butadiene)] is disclosed in U.S. Pat. No. 8,236,915.

The complexes ($^{iPr}$PDI)CoN$_2$, (Bowman A C et al., *JACS* 132:1676 (2010)), ($^{Et}$PDI)CoN$_2$, (Bowman A C et al., *JACS* 132:1676 (2010)), ($^{iPr}$BPDI)CoN$_2$, (Bowman A C et al., *JACS* 132:1676 (2010)), (MesPDI)CoCH$_3$ (Humphries, M J *Organometallics* 24:2039.2 (2005)), (Humphries, M J *Organometallics* 24:2039.2 (2005)) [($^{Mes}$PDI)CoN$_2$][MeB (C$_6$F$_5$)$_3$] (Gibson, V C et al., *J. Chem. Soc. Comm.* 2252 (2001)), and [($^{Mes}$PDI)CoCH$_3$][BArF$_{24}$] (Atienza, C C H et al., *Angew. Chem. Int. Ed.* 50:8143 (2011)) were prepared according to reported literature procedures. Phenylsilane, n-octylsilane and Et$_3$SiH were purchased from Gelest and were distilled from calcium hydride before use. The olefin substrates were dried on calcium hydride and distilled under reduced pressure before use.

$^1$H NMR spectra were recorded on Inova 400 and 500 spectrometers operating at 399.78, and 500.62 MHz, respectively. $^{13}$C NMR spectra were recorded on an Inova 500 spectrometer operating at 125.893 MHz. All $^1$H and $^{13}$C NMR chemical shifts are reported relative to SiMe$_4$ using the $^1$H (residual) and $^{13}$C chemical shifts of the solvent as a secondary standard. The following abbreviations and terms are used: bs-broad singlet; s-singlet; t-triplet; bm-broad multiplet; GC-Gas Chromatography; MS-Mass Spectroscopy; THF-tetrahydrofuran GC analyses were performed using a Shimadzu GC-2010 gas chromatograph equipped with a Shimadzu AOC-20s autosampler and a Shimadzu SHRXI-5MS capillary column (15 m×250 μm). The instrument was set to an injection volume of 1 μL, an inlet split ratio of 20:1, and inlet and detector temperatures of 250° C. and 275° C., respectively. UHP-grade helium was used as carrier gas with a flow rate of 1.82 mL/min. The temperature program used for all the analyses is as follows: 60° C., 1 min; 15° C./min to 250° C., 2 min.

Catalyst loadings in the following text are reported in mol % of the cobalt or iron complex (mol$_{complex}$/mol$_{olefin}$)×100.

Hydrosilylation Procedure: A scintillation vial was charged with weighed amounts of the olefin and silane reagents. A weighed amount of iron or cobalt pyridine diimine complex was then added to the vial, and the reaction mixture was stirred at room temperature, or at another selected temperature. Periodic monitoring of the reaction by GC and NMR spectroscopy was used to establish complete conversion of the olefin.

Example 1A, 1B and Comparative Example A

Hydrosilylation of 1-Octene with Phenylsilane

All three examples are based on the hydrosilylation of 1-octene by phenylsilane. Comparative Example A illustrates hydrosilylation catalysis by $(^{iPr}PDI)Fe(N_2)_2$ to produce phenyldioctylsilane as expected from Bart, et al (*J. Amer. Chem. Soc.*, 126 (2004) 13794-13807). Example 1A illustrates hydrosilylation catalysis with $[(^{Me}PDI)FeN_2]_2(\mu_2-N_2)$ to produce the silahydrocarbon, phenyltrioctylsilane. Example 1B illustrates synthesis of the silahydrocarbon from the reaction of 1-octene with phenyldioctylsilane produced by Comparative Example A.

Comparative Example A

The reaction was performed according to the general hydrosilylation procedure described above with 0.050 g (0.46 mmol) of phenylsilane, 0.156 g (1.36 mmol, 3 equiv) of 1-octene, and 0.002 g (0.003 mmol (0.2 mol %) of $(^{iPr}PDI)Fe(N_2)_2$. The reaction mixture was stirred for 1 hour at room temperature and quenched by exposure to air. The product mixture was analyzed by GC and NMR ($^1$H and $^{13}$C) spectroscopy. The product from the reaction was identified to be phenyldioctylsilane.

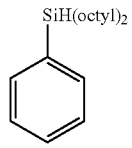

Phenyldioctylsilane. $^1$H NMR (500 MHz, CDCl$_3$): δ=0.86 (m, 4H, SiCH$_2$), 0.89 (t, 6H, CH$_3$), 1.24-1.42 (m, 24H, CH$_2$), 4.27 (quintent, 1H, SiH), 7.34-7.39 (m, 3H, p-Ph and m-Ph), 7.54 (d, 2H, o-Ph). {$^1$H} $^{13}$C NMR (125 MHz, CDCl$_3$): δ=12.05 (SiCH$_2$); 14.30 (CH$_3$); 22.85, 24.65, 29.40, 32.07, 33.44 (CH$_2$); 127.90 (m-Ph); 129.19 (p-Ph); 134.77 (o-Ph); 136.28 (i-Ph).

Example 1A

The reaction was performed according to the general hydrosilylation procedure described above using 0.050 g (0.46 mmol) of phenylsilane, 0.156 g (1.36 mmol, 3 equiv) of 1-octene and 0.002 mmol (0.1 mol %) of $[(^{Me}PDI)FeN_2]_2(\mu_2-N_2)$). The reaction mixture was stirred for 1 hour at room temperature and quenched by exposure to air. The product mixture was analyzed by GC and NMR ($^1$H and $^{13}$C) spectroscopy. The product from the reaction was identified to be phenyltrioctyl-silane.

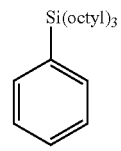

Phenyltrioctylsilane. $^1$H NMR (500 MHz, CDCl$_3$): δ=0.78 (m, 6H, SiCH$_2$), 0.89 (t, 9H, CH$_3$), 1.25-1.38 (m, 36H, CH$_2$), 7.34-7.37 (m, 3H, p-Ph and m-Ph), 7.49 (d, 2H, o-Ph). {$^1$H} $^{13}$C NMR (125 MHz, CDCl$_3$): δ=12.54 (SiCH$_2$); 14.30 (CH$_3$); 22.85, 23.92, 29.38, 29.44, 32.10, 33.99 (CH$_2$); 127.73 (m-Ph); 128.71 (p-Ph); 134.23 (o-Ph); 138.39 (i-Ph).

Example 1B

In a similar manner to the reaction of Example 1A, phenyldioctylsilane produced via Comparative Example A was reacted with 1 equivalent of 1-octene using 0.1 mol % of $[(^{Me}PDI)FeN_2]_2(\mu_2-N_2)$. The product mixture was analyzed by GC and NMR ($^1$H and $^{13}$C) spectroscopy and the reaction product was identified as phenyltrioctylsilane.

The reactions illustrated in Examples 1A, 1B and Comparative Example A can be summarized by the sequence diagrammed below.

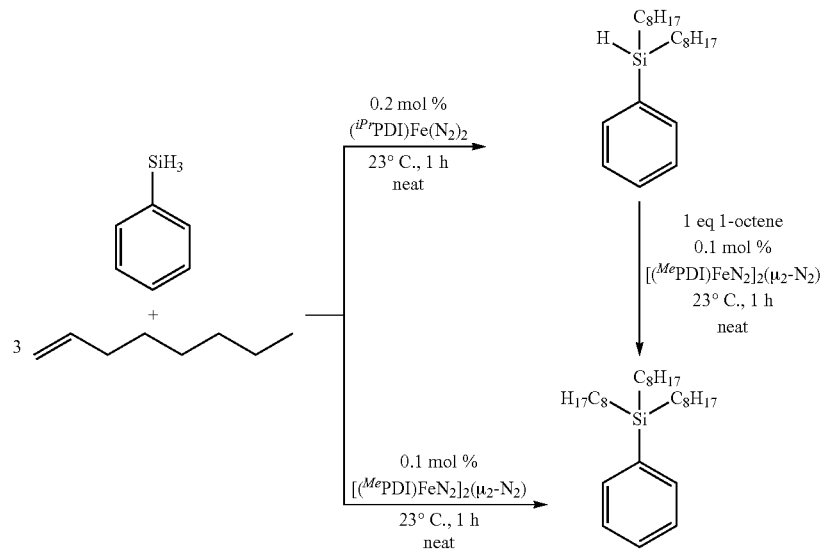

Synthesis of Phenyltrioctylsilane by Successive Hydrosilylation

Example 2A, 2B and Comparative Example B

Hydrosilylation of 1-Octene with Octylsilane

All three examples are based on the hydrosilylation of 1-octene by octylsilane. Comparative Example B illustrates hydrosilylation catalysis by $(^{iPr}PDI)Fe(N_2)_2$ to produce trioctylsilane as expected from Bart, et al (*J. Amer. Chem. Soc.*, 126 (2004) 13794-13807). Example 2A illustrates hydrosilylation catalysis with $[(^{Me}PDI)FeN_2]_2(\mu_2-N_2)$ to produce the silahydrocarbon, tetraoctylsilane. Example 2B illustrates synthesis of tetraoctylsilane from the reaction of 1-octene with trioctylsilane produced by Comparative Example B.

Comparative Example B

The reaction was performed according to the general hydrosilylation procedure described above with 0.066 g (0.46 mmol) of octylsilane, 0.156 g (1.36 mmol, 3 equiv) of 1-octene, and 0.002 g (0.003 mmol (0.2 mol %) of $(^{iPr}PDI)Fe(N_2)_2$. The reaction mixture was stirred for 1 hour at 65° C. and quenched by exposure to air. The product mixture was analyzed by GC and NMR ($^1$H and $^{13}$C) spectroscopy. The product was identified as trioctylsilane.

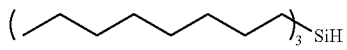

Trioctylsilane. $^1$H NMR (500 MHz, CDCl$_3$): δ=0.60 (m, 6H, SiCH$_2$), 0.91 (t, 9H, CH$_3$), 1.28-1.34 (m, 36H, CH$_2$), 3.71 (SiH). {$^1$H} $^{13}$C NMR (125 MHz, CDCl$_3$): δ=11.53 (SiCH$_2$); 14.32 (CH$_3$); 22.95, 24.94, 29.56, 29.59, 32.22, 33.68 (CH$_2$).

Example 2A

The reaction was performed according to the general hydrosilylation procedure described above with 0.066 g (0.46 mmol) of octylsilane, 0.156 g (1.36 mmol, 3 equiv) of 1-octene, and 0.002 mmol (0.1 mol %) of $[(^{Me}PDI)FeN_2]_2(\mu_2-N_2)$. The reaction mixture was stirred for 1 hour at 65° C. and quenched by exposure to air. The product mixture was analyzed by GC and NMR ($^1$H and $^{13}$C) spectroscopy. The product was identified as tetraoctylsilane.

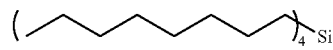

Tetraoctylsilane. $^1$H NMR (500 MHz, CDCl$_3$): δ=0.50 (m, 8H, SiCH$_2$), 0.91 (t, 12H, CH$_3$), 1.28-1.34 (m, 48H, CH$_2$). {$^1$H} $^{13}$C NMR (125 MHz, CDCl$_3$): δ=12.66 (SiCH$_2$); 14.34 (CH$_3$); 22.96, 24.16, 29.56, 29.58, 32.23, 34.21 (CH$_2$).

Example 2B

In a similar manner to the reaction of Example 2A, trioctylsilane produced via Comparative Example B was reacted with 1 equivalent of 1-octene at 65° C. using 0.1 mol % of $[(^{Me}PDI)FeN_2]_2(\mu_2-N_2)$. The product mixture was analyzed by GC and NMR ($^1$H and $^{13}$C) spectroscopy and the reaction product was identified as tetraoctylsilane.

Examples 3-10

Hydrosilylation Synthesis of Silahydrocarbons

The following Examples illustrate the hydrosilylation synthesis of various silahydrocarbons catalyzed by iron pyridine diimine complexes. The procedure used is that in Examples 1 and 2. Table 1 summarizes the quantities of raw materials employed and the products synthesized. The following catalyst abbreviations are used in the table EtPDI=$[(^{2,6-Et2}PDI)Fe(N_2)]_2[\mu-(N_2)]$,
MePDI=$[(^{2,6-Me2}PDI)Fe(N_2)]_2[\mu-(N_2)]$,
MesPDI=$[^{2,4,6-Me3}PDIFe(N_2)]_2[(\mu-N_2)]$,
PrBtdPDI=$[^{2,6-iPr2}PDIFe(butadiene)]$

TABLE 1

Hydrosilylation Synthesis of the Silahydrocarbons of Examples 3-10

| EX | SILANE | Alpha-OLEFIN | CATALYST | TEMP °C./TIME, h | PRODUCT |
|---|---|---|---|---|---|
| 3 | C$_6$H$_5$SiH$_3$, 0.5 mmol | C$_8$H$_{16}$, 1.51 mmol | MesPDI, 1 mol % | 23, 1 h | Phenyltrioctylsilane |
| 4 | C$_6$H$_5$SiH(C$_8$H$_{17}$)$_2$, 0.46 mmol | C$_8$H$_{16}$, 0.46 mmol | MesPDI, 1 mol % | 23, 1 h | Phenyltrioctylsilane |
| 5 | C$_8$H$_{17}$SiH$_3$, 0.5 mmol | C$_{10}$H$_{20}$, 1.5 mmol | MePDI, 0.1 mol % | 65, 1 h | Octyltridecylsilane |
| 6 | C$_8$H$_{17}$SiH$_3$, 0.5 mmol | C$_{18}$H$_{36}$, 1.55 mmol | EtPDI, 0.2 mol % | 65, 1 h | Octyltris(octadecyl)silane |
| 7 | C$_6$H$_{13}$(C$_{10}$H$_{21}$)SiH$_2$, 0.49 mmol | C$_{14}$H$_{28}$, 1.0 mmol | MePDI, 0.2 mol % | 23, 1 h | Hexyldecylbis(tetradecyl)silane |
| 8 | C$_6$H$_5$SiH$_3$, 0.5 mmol | C$_8$H$_{16}$, 0.5 mmol and C$_{10}$H$_{20}$, 1.0 mmol | MePDI, 0.2 mol % | 23, 1 h | Phenyloctyldidecylsilane |
| 9 | C$_8$H$_{17}$SiH$_3$, 0.46 mmol | C$_6$H$_{12}$, 1.0 mmol and C$_{18}$H$_{36}$, 0.5 mmol | MePDI, 0.2 mol % | 65, 1 h | Octyldihexyloctadecylsilane |
| 10 | (C$_2$H$_5$)$_3$SiH, 0.5 mmol | C$_8$H$_{16}$, 0.25 mmol and C$_{18}$H$_{36}$, 0.25 mmol | PrBtdPDI, 1 mol % | 23, 24 h | Octyltriethylsilane and Octadecyltriethylsilane |

Triethyloctylsilane. $^1$H NMR (C6D6, 22° C.): 1.39-1.28 (m, 12H), 0.99 (t, 9H, J=7.9 Hz), 0.93 (t, 3H, 8.6 Hz), 0.97 (t, 9H, 8 Hz), 0.59-0.51 (m, 8H). $^{13}$C NMR: 34.83, 32.79, 30.21, 30.19, 24.73, 23.53, 14.77, 12.08, 8.16, 4.08.

Examples 11A-11B

Catalytic Synthesis of Unsaturated Silahydrocarbons

These Examples illustrate the catalytic synthesis of unsaturated silahydrocarbons using cobalt-containing compounds of Formula (III).

Example 11A

Synthesis of 1-Triethylsilyl-2-octene, $(C_2H_5)_3Si(CH_2CH=CHC_5H_{11})$

In a nitrogen-filled drybox, a scintillation vial was charged with 0.100 g (0.891 mmol) of 1-octene and 0.449 mmol (0.5 equiv) of 0.052 g Et$_3$SiH. 0.001 g (0.002 mmol, 0.5 mol %) of ($^{Mes}$PDI)CoMe was then added to the mixture and the reaction was stirred at room temperature (23° C.) for 24 hours. The reaction was quenched by exposure to air, and the product mixture was analyzed by gas chromatography and $^1$H and $^{13}$C NMR spectroscopy. Conversion of the SiH and olefin functional groups was greater than 99%. GC analysis showed 46% of the alkenylsilane and 52% octane. Both E and Z isomers of 1-triethylsilyl-2-octene were formed. The alkenylsilane product was purified by passing the mixture through a silica gel column with hexane followed by removal of the volatiles in vacuo. In another experiment, during which the progress of the reaction was monitored by NMR, 37% conversion occurred in 30 minutes at 23° C. Product distribution at that point was 36% E isomer, 21% Z isomer and 41% octane. The $^1$H and $^{13}$C NMR details of 1-triethylsilyl-2-octene are presented below.

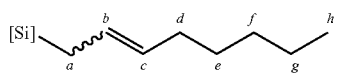

1-Triethylsilyl-2-octene. $^1$H NMR (benzene-d$_6$): δ=0.55 (t, 6H, Si(CH$_2$CH$_3$)$_3$), 0.91 (t, 3H, H$^h$), 0.97 (t, 9H, Si(CH$_2$CH$_3$)$_3$), 1.28 (m, 2H, H$^f$), 1.32 (m, 2H, H$^g$), 1.36 (m, 2H, H$^e$), 1.50 (d, 2H {75%}, H$^a$-trans isomer), 1.54 (d, 2H {25%}, H$^a$-cis isomer), 2.03 (m, 2H {75%}, H$^d$-trans isomer), 2.08 (m, 2H {25%}, H$^d$-cis isomer), 5.47 (m, 1H {75%}, H$^c$-trans isomer), 5.50 (m, 1H {25%}, H$^c$-cis isomer), 5.36 (m, 1H {75%}, H$^b$-trans isomer), 5.38 (m, 1H {25%}, H$^b$-cis isomer). $^{13}$C {$^1$H} NMR (benzene-d$_6$): δ=2.82 (Si(CH$_2$CH$_3$)$_3$), 7.70 (Si(CH$_2$CH$_3$)$_3$), 14.42 (C$^h$), 17.70 (C$^a$-trans), 17.71 (C$^a$-cis), 23.04 (C$^g$), 23.19 (C$^e$), 29.24 (C$^f$), 32.40 (C$^d$-trans), 32.47 (C$^d$-cis), 126.41 (C$^b$-trans), 126.46 (C$^b$-cis), 129.31 (C$^c$-trans), 129.33 (C$^c$-cis).

Example 11B

This Example illustrates the synthesis of 1-triethylsilyl-2-octene with ($^{Mes}$PDI)CoN$_2$ as the catalyst. The experiment of Example 11 was repeated with 0.447 mmol (0.052 g) (C$_2$H$_5$)$_3$SiH, 0.89 mmol 1-octene and 0.004 g ($^{Mes}$PDI)CoN$_2$. After 24 hours at 23° C., the reaction mixture was analyzed and found to contain 45% of the alkenylsilane and 43% octane. Conversion was 88%.

Example 12

Synthesis of Bis(Alkenyl)Silanes from Internal Olefins

This Example illustrates the synthesis of bis(alkenyl)silanes from internal olefins. The experiment was carried out in a manner similar to that of Example 11A with 0.100 g (0.891 mmol) of cis- or trans-4-octene and 0.009 mmol (1 mol %) of the cobalt complex (0.004 g of ($^{Mes}$PDI)CoCH$_3$), and 0.447 mmol (0.5 equiv) of the (C$_2$H$_5$)$_3$SiH (0.052 g). The reactions were stirred at room temperature for 24 hours and then quenched by exposure to air and the product mixtures were analyzed by gas chromatography and NMR spectroscopy. Results showed 70% conversion for cis-4-octene and 85% conversion for trans-4-octene. NMR indicated that, in both reactions, silylation had occurred primarily at the terminal carbon.

Example 13

Use of Cobalt Pyridine Diimine Complexes

This Example illustrates the use of cobalt pyridine diimine complexes to synthesize bis(alkenyl)silanes from primary silanes and alpha olefins.

Dehydrogenative silylation with C$_6$H$_5$SiH$_3$. This reaction was performed using the general procedure for the silylation of 1-octene described in Example 11. 0.002 g (0.004 mmol, 1 mol %) of ($^{Mes}$PDI)CoMe, 0.050 g (0.46 mmol) of PhSiH$_3$ and 0.207 g (1.85 mmol, 4 equiv) of 1-octene were used, and the reaction was run at 23° C. for 1 h. Complete conversion to C$_6$H$_5$(2-octenyl)$_2$SiH (2:1 E/Z) was observed by GC and NMR spectroscopy.

bis(2-octenyl)phenylsilane. $^1$H NMR (500 MHz, CDCl$_3$): δ=0.88 (t, 3H, C$^8$H$_3$), 1.16-1.35 (m, 6H, C$^5$H$_2$C$^6$H$_2$C$^7$H$_2$), 1.81 (d, 7.3 Hz, 4H {67%}, C$^1$H$_2$-E isomer), 1.84 (d, 8.3 Hz, 4H {33%}, C$^1$H$_2$-Z isomer), 1.94 (m, 2H, C$^4$H$_2$), 4.15 (s, 1H, SiH), 5.30 (m, 1H, C$^3$H), 5.40 (m, 1H, C$^2$H), 7.33-7.44 (m, 3H, p-Ph and m-Ph), 7.53 (d, 2H, o-Ph). {$^1$H} $^{13}$C NMR (125 MHz, CDCl$_3$): δ=14.42 (C$^8$-E), 15.11 (C$^8$-Z), 16.13 (C$^1$-Z), 16.36 (C$^1$-E), 22.67 (C$^7$-Z), 22.84 (C$^7$-E), 29.47 (C$^5$-E), 29.53 (C$^5$-Z), 31.77 (C$^6$-Z), 31.99 (C$^6$-E), 32.66 (C$^4$-Z), 32.84 (C$^4$-E), 124.46 (C$^2$-Z), 125.25 (C$^2$-E), 127.79 (m-Ph), 127.82 (p-Ph), 129.04 (C$^3$-Z), 129.29 (C$^3$-E), 134.65 (i-Ph), 135.29 (o-Ph).

Example 14A-14D

Synthesis of Unsaturated Silahydrocarbons

This Example illustrates synthesis of unsaturated silahydrocarbons by reacting a stoichiometric excess of olefins with the bis(alkenyl)silanes of Example 13A in the presence of the iron pyridine diimine catalysts of U.S. Pat. No. 8,236,915. The catalyst source is 1 mol % [($^{2,6-Me2}$PDI)Fe(N$_2$)]$_2$[μ-(N$_2$)]. Reactions and products are summarized in the table below.

TABLE 2

| Reagents and Products of Example 14A-14D | | | |
|---|---|---|---|
| EXAMPLE | SILANE | OLEFIN | PRODUCT |
| 14A | C$_6$H$_5$(2-octenyl)$_2$SiH | Hexene | Phenyl-hexylbis(2-octenyl)-silane |

TABLE 2-continued

Reagents and Products of Example 14A-14D

| EXAMPLE | SILANE | OLEFIN | PRODUCT |
|---|---|---|---|
| 14B | $C_6H_5$(2-octenyl)$_2$SiH | Decene | Phenyl-decylbis(2-octenyl)-silane |
| 14C | $C_8H_{17}$(2-octenyl)$_2$SiH | Octadecene | Phenyl-octadecylbis(2-octenyl)silane |
| 14D | $C_8H_{17}$(2-octenyl)$_2$SiH | Octene | Phenyl-octylbis(2-octenyl)-silane |

Example 15A-15G

Synthesis of Polysilahydrocarbon Compounds

This Example illustrates the synthesis of polysilahydrocarbon compounds with the iron pyridine diimine complex, $[(^{2,6\text{-}Me2}PDI)Fe(N_2)]_2[\mu\text{-}(N_2)]$, as the catalyst source. The general procedure for the experiments is described in Examples 1 and 2. The silanes, unsaturated substrates and products are identified in Table 3. In Examples 15A-15D and 15F, unsaturation is internal, but it is terminal in Examples 15E and 15G.

TABLE 3

Synthesis of Disila- (Examples 15A, 15B), Trisila- (Example 15C), Tetrasila- (Examples 15D-15F) and Pentasila-hydrocarbon (Example 15G) Compounds

| Ex | Reactions And Products |
|---|---|
| 15A | $(C_2H_5)_3Si(CH_2CH=CHC_5H_{11}) + (C_2H_5)_3SiH \rightarrow$ $(C_2H_5)_3Si(CH_2)_8Si(C_2H_5)_3$ |
| 15B | $(C_2H_5)_3Si(CH_2CH=CHC_5H_{11}) + C_6H_5(C_8H_{17})_2SiH \rightarrow$ $C_6H_5(C_8H_{17})_2Si(CH_2)_8Si(C_2H_5)_3$ |
| 15C | $C_6H_5CH_3Si(CH_2CH=CHC_5H_{11})_2 + 2C_6H_5(CH_3)_2SiH \rightarrow$ $C_6H_5CH_3Si[(CH_2)_8SiC_6H_5(CH_3)_2]_2$ |
| 15D | $C_6H_5SiH_3 + 3(C_2H_5)_3Si(CH_2CH=CHC_5H_{11}) \rightarrow$ $C_6H_5Si[(CH_2)_8Si(C_2H_5)_3]_3$ |
| 15E | $C_6H_{13}SiH_3 + 3H_2C=CHCH_2Si(C_4H_9)_3 \rightarrow$ $C_6H_{13}Si[C_3H_6Si(C_4H_9)_3]_3$ |
| 15F | $C_8H_{17}SiH_3 + 3CH_3CH=CHSi(C_{10}H_{21})_3 \rightarrow$ $C_8H_{17}Si[C_3H_6Si(C_{10}H_{21})_3]_3$ |
| 15G | $4(C_{12}H_{25})_3SiH + Si(C_2H_3)_4 \rightarrow Si[C_2H_4Si(C_{12}H_{25})_3]_4$ |

While the above description contains many specifics, these specifics should not be construed as limitations on the scope of the invention, but merely as exemplifications of preferred embodiments thereof. Those skilled in the art may envision many other possible variations that are within the scope and spirit of the invention as defined by the claims appended hereto.

What is claimed is:

1. A process for the production of silahydrocarbons, comprising:
reacting at least one first reactant with at least one second reactant in the presence of a catalyst, to produce silahydrocarbons having the general formulae $R^1R^2R^3R^4Si$, $R^1R^2R^3Si(Q)SiR^1R^2R^3$, $R^5R^6R^7R^8Si$, $R^5R^6R^7Si(Q)SiR^5R^7R^8$, $(R^1)_2Si[QSi(R^1)_3]_2$, $R^1Si[QSi(R^1)_3]_3$, or $Si[QSi(R^1)_3]_4$, wherein $R^1$, $R^2$, $R^3$, $R^4$, $R^5$, $R^6$, $R^7$, and $R^8$ are selected from the group consisting of aliphatic, aryl, alkaryl, aralkyl, and cycloaliphatic univalent hydrocarbyl groups having from one to thirty carbon atoms, with the proviso that at least one of $R^5$, $R^6$, $R^7$, or $R^8$ has an alkenyl functional group; and Q is a straight or branched alkylene group having from two to twenty carbon atoms;

wherein the first reactant is selected from the group consisting of olefins of 2 to 30 carbon atoms and alkenylsilanes of general formulae $(R^1)_2Si(R^k)_2$, $(R^1)_3Si(R^k)$, $(R^1)Si(R^k)_3$, $Si(R^k)_4$ or a combination of two or more thereof, wherein $R^k$ is an alkenyl group of two to thirty carbons and $R^1$ is an aliphatic, aryl, alkaryl, aralkyl, and cycloaliphatic univalent hydrocarbyl groups having from one to thirty carbon atoms;

wherein the second reactant is selected from the group consisting of (i) a monosilane ($SiH_4$) and hydridosilanes of general formulae, $R'SiH_3$, $(R')_2SiH_2$, or $(R')_3SiH$, or $(R')_nH_{3-n}SiQSi(R')_yH_{3-y}$ wherein n is 0, 1, 2, or 3, y is 0, 1, 2, or 3, n+y≥1 $R'$ is an aliphatic, aryl, alkaryl, aralkyl, and cycloalpihatic univalent hydrocarbyl group having from one to thirty carbon atoms, or a combination of two or more thereof, or (ii) an alkenyl silane of the formula $(R^1)(R^k)_2SiH$, $(R^1)_2(R^k)SiH$, or a combination thereof, wherein $R^k$ is an alkenyl group of two to thirty carbons and $R^1$ is an aliphatic, aryl, alkaryl, aralkyl, and cycloaliphatic univalent hydrocarbyl groups having from one to thirty carbon atoms, or a combination of two or more thereof; and wherein the catalyst is selected from the group consisting of an iron complex of Formula (I), an iron complex of Formula (II), or a cobalt complex of Formula (III):

FORMULA (I)

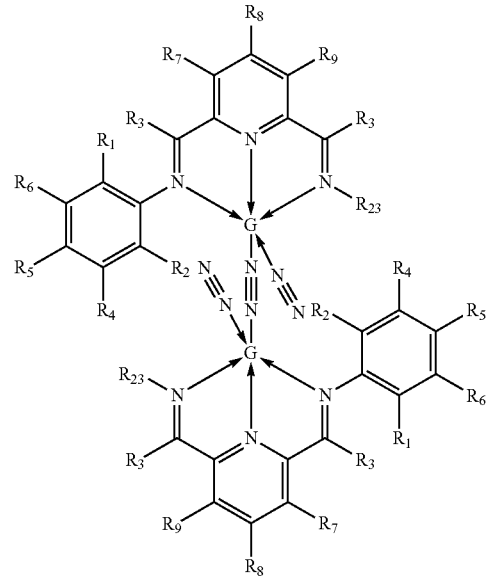

FORMULA (II)

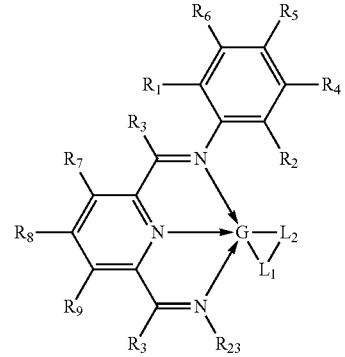

-continued

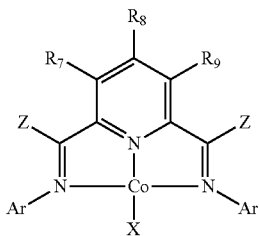

Formula (III)

wherein:

G is Fe;

each occurrence of $R_1$, $R_2$, $R_3$, $R_4$, $R_5$, $R_6$, $R_7$, $R_8$, and $R_9$ is independently hydrogen, C1-C18 alkyl, C1-C18 substituted alkyl, aryl, substituted aryl, or an inert substituent, wherein $R_2$-$R_9$, other than hydrogen, optionally contain at least one heteroatom;

each occurrence of $R_{23}$ is independently C1-C18 alkyl, C1-C18 substituted alkyl, aryl or substituted aryl, wherein $R_{23}$ optionally contains at least one heteroatom; optionally, any two of $R_1$, $R_2$, $R_3$, $R_4$, $R_5$, $R_6$, $R_7$, $R_8$, $R_9$, and $R_{23}$ vicinal to one another taken together may form a ring being a substituted or unsubstituted, saturated, or unsaturated cyclic structure wherein $L_1$-$L_2$ is

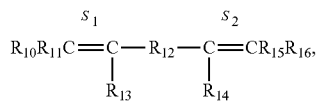

Formula (A)

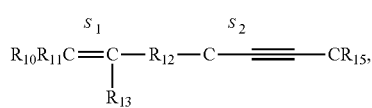

Formula (B)

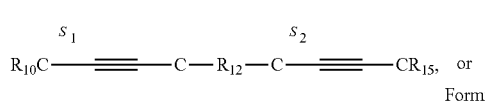

Formula (C)

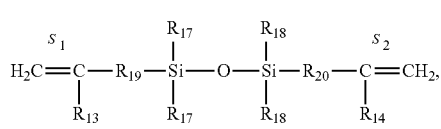

Formula (D)

wherein each occurrence of $R_{10}$, $R_{11}$, $R_{13}$, $R_{14}$, $R_{15}$, and $R_{16}$ is independently hydrogen, C1-C18 alkyl, C2-C18 alkenyl, or C2-C18 alkynyl, wherein $R_{10}$, $R_{11}$, $R_{13}$, $R_{14}$, $R_{15}$, and $R_{16}$, other than hydrogen, optionally contain at least one heteroatom, and $R_{10}$, $R_{11}$, $R_{13}$, $R_{14}$, $R_{15}$, and $R_{16}$, other than hydrogen, are optionally substituted, each occurrence of $R_{12}$ is independently C1-C18 alkylene, C1-C18 substituted alkylene, C2-C18 alkenylene, C2-C18 substituted alkenylene, C2-C18 alkynylene, C2-C18 substituted alkynylene, arylene, substituted arylene, wherein $R_{12}$ optionally contains at least one heteroatom;

optionally any two of $R_{10}$, $R_{11}$, $R_{12}$, $R_{13}$, $R_{14}$, $R_{15}$, $R_{16}$ taken together form a ring being a substituted or unsubstituted, saturated or unsaturated cyclic structure;

each occurrence of $R_{17}$ and $R_{18}$ is independently alkyl, substituted alkyl, aryl, or substituted aryl, wherein each of $R_{17}$ and $R_{18}$ optionally contains at least one heteroatom, and wherein $R_{17}$ and $R_{18}$ taken together optionally form a ring being a substituted or unsubstituted, saturated or unsaturated cyclic structure;

each occurrence of $R_{19}$ and $R_{20}$ is independently a covalent bond that connects Si and C, an alkylene, substituted alkylene, or a heteroatom, wherein $R_{19}$ and $R_{20}$ optionally contain at least one heteroatom;

wherein $L_1$-$L_2$ bonds with G through unsaturated sites $S_1$ and $S_2$;

each occurrence of Ar is independently C1-C18 alkyl, C1-C18 substituted alkyl, aryl or substituted aryl, wherein Ar optionally contains at least one heteroatom;

Z is independently hydrogen, C1-C18 alkyl, C1-C18 substituted alkyl, aryl, substituted aryl, or an inert substituent;

$R_7$, $R_8$ and $R_9$ are independently hydrogen, C1-C18 alkyl, C1-C18 substituted alkyl, aryl, substituted aryl, or an inert substituent;

X is $N_2$, CO, alkyl, OH, SH, SeH, —H, or $SiR_3$ where R is an alkyl, aryl, or siloxanyl group;

with the provisos that (1) $R_1$ in Formula (I) is hydrogen, methyl, ethyl or n-propyl;

(2) $L_1$-$L_2$ of Formula (A) is selected from the group consisting of 1,3-divinyltetramethyldisiloxane, 1,3-butadiene, 1,5-cyclooctadienes, dicyclopentadienes, and norbornadienes;

(3) the second reactant is selected from a silane of (i) or (ii) when the catalyst is a compound of Formula (III); and (4) the second reactant is selected from a silane of Formula (ii) when the catalyst is a compound of Formula (I) or (II).

2. The process of claim 1, wherein $R^1$, $R^2$, $R^3$, $R^4$, $R^5$, $R^6$, $R^7$, and $R^8$ are independently selected from the group consisting of hydrogen, methyl, ethyl, octyl, octadecyl, phenyl, phenylethyl, and cyclohexylpropyl groups.

3. The process of claim 1, wherein the silahydrocarbon produced by the process is selected from the group consisting of methyltri(octyl)silane, dimethyl(dioctyl)silane, methyl(hexyl)(decyl)octadecylsilane, tetra(octyl)silane, phenyltri(octyl)silane, phenyl(dipentyl)dodecylsilane, phenyl(dinonyl)butylsilane, octyltridecylsilane, octyltris(octadecyl)silane, hexyldecylbis(tetradecly)silane, phenyloctyldidecylsilane, octyldihexyloctadecylsilane, octyltriethylsilane, and/or octadecyltriethylsilane.

4. The process of claim 1, wherein the silahydrocarbon produced by the process is selected from the group consisting of dimethyldi(decenyl)silane, dioctlyldi(tetradecenyl)silane, methyl(octyl)di-(hexenyl)silane, phenyl(nonyl)di(dodecenyl)silane, octyl(decyl)(octenyl)-(decenyl)silane, triethylocteylsilane, phenyl(heptyl)(nonenyl)(undecenyl)silane, tri(octyl)(hexadecenyl)silane, cyclohexyl(phenethyl)(heptyl)(nonenyl)silane, methyl(hexyl)(decyl)(dodecenyl)silane, ethyldi(pentyl)(tetradecenyl)silane, phenylhexylbis(2-octenyl)silane, phenyldecylbis(2-octenyl)silane, phenyloctadecylbis(2-octenyl)silane, and/or phenyoctylbis(2-octenyl)silane.

5. The process of claim 1, wherein the silahydrocarbon produced by the process is a polysilahydrocarbon selected from the group consisting of $(C_2H_5)_3Si(CH_2)_8Si(C_2H_5)_3$, $C_6H_5(C_8H_{17})_2Si(CH_2)_8Si(C_2H_5)_3$, $C_6H_5CH_3Si[(CH_2)_8SiC_6H_5(CH_3)_2]_2$, $C_6H_5Si[(CH_2)_8Si(C_2H_5)_3]_3$, $C_6H_{13}Si[C_3H_6Si(C_4H_9)_3]_3$, $C_8H_{17}Si[C_3H_6Si(C_{10}H_{21})_3]_3$, or $Si[C_2H_4Si(C_{12}H_{25})_3]_4$.

6. The process of claim 1, wherein said first reactant is an olefin of 2 to 30 carbon atoms and said second reactant is selected from the group consisting of primary silanes of general formula, R'SiH$_3$, secondary silanes of general formula, (R')$_2$SiH$_2$, and tertiary silanes of general formula, (R')$_3$SiH.

7. The process of claim 1, wherein said first reactant is an olefin of 2 to 30 carbon atoms and said second reactant is selected from the group consisting of alkylbis(alkenyl)silanes and arylbis(alkenyl)silanes of formula, R$^1$(R$^k$)$_2$SiH, and alkenylbis(alkyl)silanes and arylalkenylalkylsilanes of formula, (R$^1$)$_2$R$^k$SiH.

8. The process of claim 1, wherein said catalyst of Formula (I) is [($^{2,6-(R'')2}$PDI)Fe(N$_2$)]$_2$(μ$_2$-N$_2$), where R" represents R$_1$ and/or R$_2$ in Formula (I).

9. The process of claim 8, wherein R" is independently chosen from methyl, ethyl, and mesityl.

10. The process of claim 1, wherein the catalyst of Formula (II) is selected from the group consisting of ($^{2,6-(R'')2}$PDI)Fe(M$^{vi}$M$^{vi}$) and ($^{2,6-(R'')2}$PDI)Fe(H$_2$C=CHCH=CH$_2$), where R" represents R$_1$ and R$_2$ in Formula (II).

11. The process of claim 10, wherein R" is independently chosen from methyl, ethyl, and mesityl.

12. The process of claim 1, wherein the reaction temperature is 0-300° C.

13. The process of claim 1, wherein the reaction temperature is 20-100° C.

14. The process of claim 1, wherein the catalyst is present in an amount of from about 0.01 mole percent to about 10 mole percent based on the quantity of the olefins.

15. The process of claim 1, wherein the catalyst is present in an amount of from about 0.1 mole percent to about 5 mole percent based on the quantity of the olefins.

16. The process of claim 1, wherein the catalyst of Formula (III) is selected from the group consisting of ($^{Mes}$PDICoCH$_3$), ($^{Mes}$PDIMeCoCH$_3$), ($^{2,6-iPr}$PDICoN$_2$) ($^{2,6-iPr}$PDIMeCoN$_2$) ($^{2,6-iPr}$PDIPhCoN$_2$), ($^{2,6-iPr}$PDIMeCoOH), ($^{Mes}$PDI)CoOH, ($^{2,6-Et}$PDI)CoN$_2$, and ($^{2,6-iPr}$BPDI)CoN$_2$.

17. A process for hydrosilylation/dehydrogenative silylation synthesis comprising reacting C2-C30 olefins and primary silanes of general formula, R'SiH$_3$ or monosilane (SiH$_4$) in the presence of the catalyst of Formula (III)

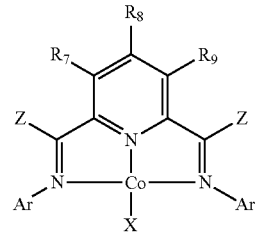

Formula (III)

wherein:
each occurrence of Ar is independently C1-C18 alkyl, C1-C18 substituted alkyl, aryl or substituted aryl, wherein Ar optionally contains at least one heteroatom;
Z is independently hydrogen, C1-C18 alkyl, C1-C18 substituted alkyl, aryl, substituted aryl, or an inert substituent;
R$_7$, R$_8$ and R$_9$ are independently hydrogen, C1-C18 alkyl, C1-C18 substituted alkyl, aryl, substituted aryl, or an inert substituent;
X is N$_2$, CO, alkyl, OH, SH, SeH, —H, or SiR$_3$ where R is an alkyl, aryl, or siloxanyl group;
to produce alkylbis(alkenyl)-silanes and arylbis(alkenyl) silanes of formula, R$^1$(R$^k$)$_2$SiH, alkenylbis(alkyl)silanes and arylalkenylalkylsilanes of formula, (R$^1$)$_2$R$^k$SiH, or tetralkenylsilanes of general formula Si(R$^k$)$_4$, wherein R$^1$ is an aliphatic, aryl, alkaryl, aralkyl, and cycloaliphatic univalent hydrocarbyl groups having from one to thirty carbon atoms; R' is an aliphatic, aryl, alkaryl, aralkyl, and cycloaliphatic univalent hydrocarbyl group having from one to thirty carbon atoms such as methyl, ethyl, octyl, octadecyl, phenyl, tolyl, phenylethyl, mesityl and cyclohexylpropyl; and R$^k$ is an alkenyl group of two to thirty carbons.

18. The process of claim 17, wherein the catalyst of Formula (III) is selected from the group consisting of ($^{Mes}$PDICoCH$_3$), ($^{Mes}$PDIMeCoCH$_3$), ($^{2,6-iPr}$PDICoN$_2$) ($^{2,6-iPr}$PDIMeCoN$_2$) ($^{2,6-iPr}$PDIPhCoN$_2$), ($^{2,6-iPr}$PDIMeCoOH), ($^{Mes}$PDI)CoOH, ($^{2,6-Et}$PDI)CoN$_2$, and ($^{2,6-iPr}$BPDI)CoN$_2$.

19. The process of claim 17, wherein the reaction temperature is 0-300° C.

20. The process of claim 17, wherein the reaction temperature is 20-100° C.

* * * * *